(12) United States Patent
Kool et al.

(10) Patent No.: US 7,745,614 B2
(45) Date of Patent: Jun. 29, 2010

(54) UNIVERSAL LINKER COMPOSITIONS FOR THE RELEASE OR TRANSFER OF CHEMICAL AGENTS FROM A POLYNUCLEOTIDE

(75) Inventors: Eric Todd Kool, Stanford, CA (US); Hiroshi Abe, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 907 days.

(21) Appl. No.: 11/218,961

(22) Filed: Sep. 1, 2005

(65) Prior Publication Data

US 2006/0199192 A1 Sep. 7, 2006

Related U.S. Application Data

(60) Provisional application No. 60/607,226, filed on Sep. 3, 2004.

(51) Int. Cl.
| | |
|---|---|
| *C07H 21/02* | (2006.01) |
| *C07H 19/04* | (2006.01) |
| *C12Q 1/68* | (2006.01) |
| *C07H 21/00* | (2006.01) |
| *C07F 9/00* | (2006.01) |

(52) U.S. Cl. .................. 536/26.6; 536/4.1; 536/23.1; 536/25.3; 536/23.32; 532/1; 564/12; 977/792; 435/6

(58) Field of Classification Search .................. 532/1; 564/12; 536/4.1, 23.1, 25.3, 26.6, 23.32; 977/792; 435/6; 514/51
See application file for complete search history.

(56) References Cited

U.S. PATENT DOCUMENTS

| | | | |
|---|---|---|---|
| 4,958,013 A | 9/1990 | Letsinger | |
| 5,571,903 A | 11/1996 | Gryaznov | |
| 7,109,312 B2 * | 9/2006 | Cook et al. | ................. 534/558 |

FOREIGN PATENT DOCUMENTS

WO    WO 2004/010101    1/2004

OTHER PUBLICATIONS

Stratagene Catalog p. 39, 1988.*

(Continued)

*Primary Examiner*—Jezia Riley
(74) *Attorney, Agent, or Firm*—Bozicevic, Field & Francis LLP; Pamela J. Sherwood

(57) ABSTRACT

A universal linker structure is provided, in which a functional group and activating leaving group are placed on a tether, allowing the placement of an electrophile at the end of any nucleic acid sequence. The electrophile on the tether can react with a second nucleic acid carrying a nucleophile when the two nucleic acids are hybridized near one another, resulting in release of the leaving group, and creation of a functional change. The linker can be designed to destabilize the ligation product without slowing the rate of reaction. This lowers product inhibition, and the target DNA or RNA can become a catalyst for isothermally generating multiple signals for detection. This enhanced signal is demonstrated in solution experiments and in solid supported assays. The universal linkers of the present invention are simple and inexpensive to prepare, and can be appended to any polynucleotide in automated steps on a standard DNA synthesizer.

15 Claims, 10 Drawing Sheets

OTHER PUBLICATIONS

Brunner et al., DNA-Templated Metal Catalysis, J. Am. Chem. Soc., 2003, 125, 12410-12411.

Ficht et al., Single-Nucleotide-Specific PNA—Peptide Ligation on Synthetic and PCR DNA Templates, 2004, JACS, 126:9970-9981.

Gryaznov et al., Chemical Ligation of Oligonucleotides in the Presence and Absence of a Template, 1993, JACS 115:3808-3809.

Komatsu et al., In Vitro Selection of Hairpin Ribozymes Activated with Short Oligonucleotides, Biochemistry, 2002, 41, 9090-9098.

Kuhn et al., Brief Communication PNA Beacons for Duplex DNA, 2001, Antisense Nucleic Acid Drug Dev., 2001, 11:265-270.

Luther et al., Surface-promoted replication and exponential amplification of DNA analogues, Nature, 1998, 396, 245-248.

Ma et al., PNA-Based RNA-Triggered Drug-Releasing System, Bioconjugate Chem., 2003, 14, 679-683.

Ma et al., Nucleic Acid Triggered Catalytic Drug and Probe Release: A New Concept for the Design of Chemotherapeutic and Diagnostic Agents, Bioorg. Med. Chem., 2001, 9, 2501-2510.

Ma et al., Nucleic acid-triggered catalytic drug release, Proc. Natl. Acad. Sci., 2000, 97(21), 11159-11163.

Okamoto et al., Design of Base-discriminating Fluorescent Nucleoside and its Application to T/C SNP Typing, 2003, JACS, 125:9296-9297.

Paris et al., Probing DNA sequences in solution with a monomer-excimer fluorescence color change, 1998, N.A.R., 26:3789-3793.

Sando et al., Quencher as Leaving Group: Efficient Detection of DNA-Joining Reactions, 2002, J. Am. Chem. Soc., 124 (10): 2096-2097.

Sando et al., Amplified Nucleic Acid Sensing Using Programmed Self-Cleaving DNAzyme, J. Am. Chem. Soc., 2003, 125, 15720-15721.

Tyagi et al., Molecular Beacons: Probes that Fluoresce upon Hybridization, 1996, Nat. Biotech., 14:303-308.

Wang et al., A Novel Mode of Regulation of an RNA-cleaving DNAzyme by Effectors that Bind to Both Enzyme and Substrate, J. Mol. Biol., 2001, 310, 723-734.

Xu et al., A Novel 5'-Iodonucleoside Allows Efficient Nonenzymatic Ligation of Single-stranded and Duplex DNAs, 1997, Tetrahedron Lett., 38:5595-5598.

Xu et al., Rapid and Selective Selenium-Mediated Autoligation of DNA Strands, 2000, JACS, 122:9040-9041.

Xu et al., Nonenzymatic autoligation in direct three-color detection of RNA and DNA point mutations, 2001, Nat. Biotech., 19:148-152.

Zhan et al., Chemical Amplification through Template-Directed Synthesis, J. Am. Chem. Soc., 1997, 119, 12420-12421.

\* cited by examiner

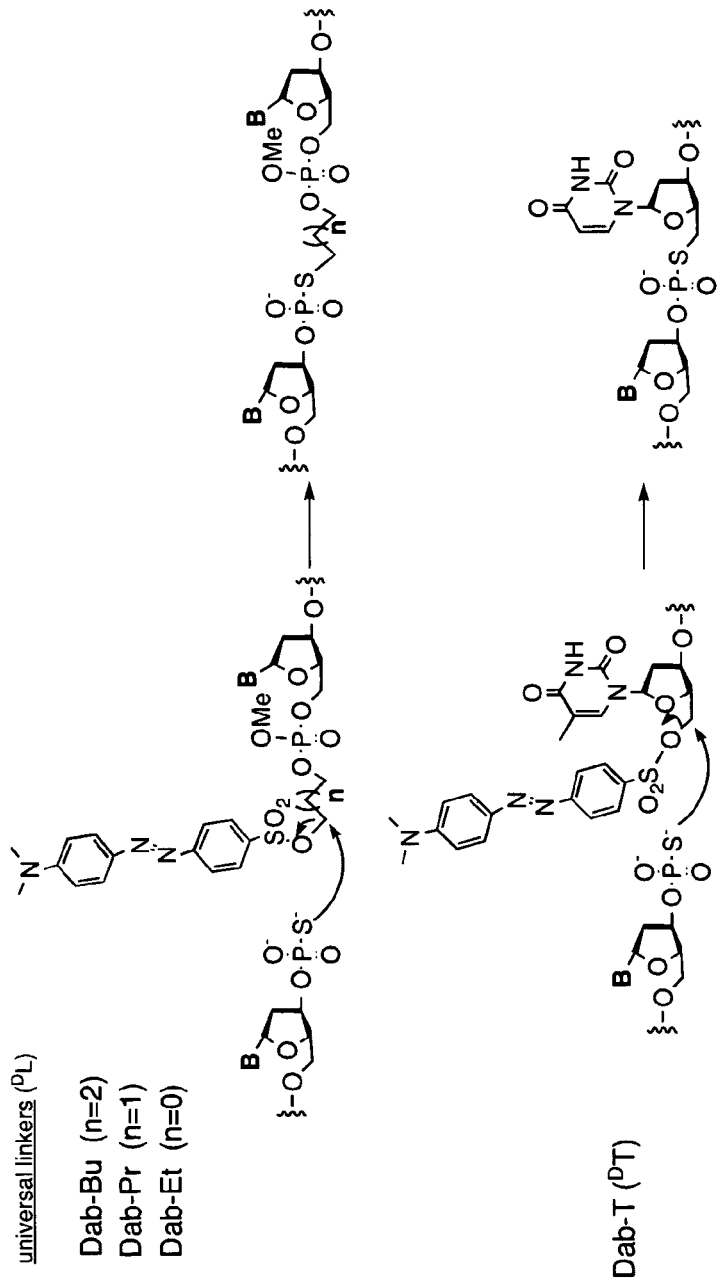

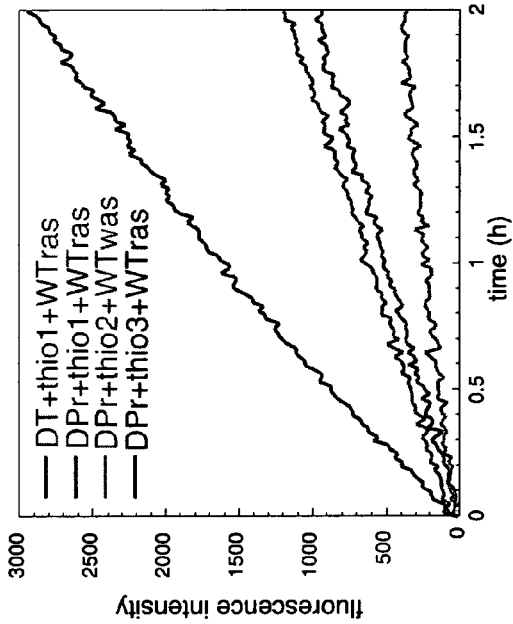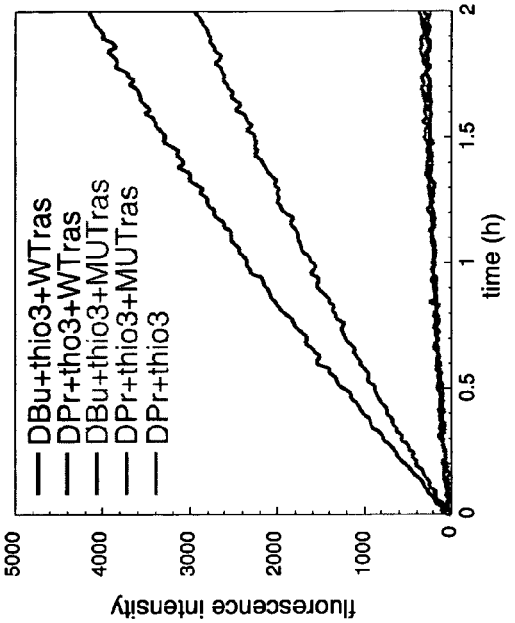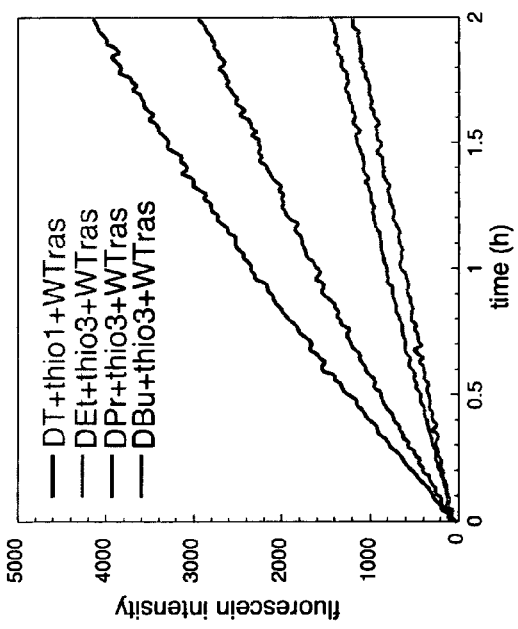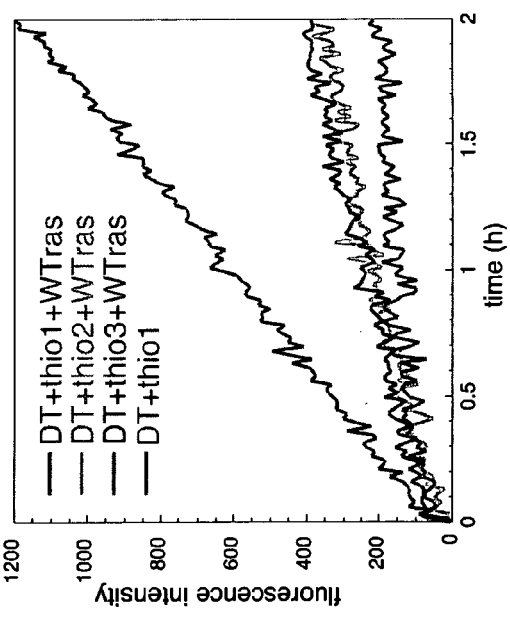
FIG. 2A
FIG. 2B
FIG. 2C
FIG. 2D

FIG. 3

| | | |
|---|---|---|
| Thio4 | $^5$CGGTGCG$_S$ $^D$L-TGTGGGCA$_{3'}$ | Bu40 |
| Thio5 | $^5$GGTGCG$_S$ $^D$L-GTGTGGGC$_{3'}$ | Bu41 |
| Thio6 | $^5$CGTGCGGGTGCG$_S$ $^D$L-GTGGGCAA$_{3'}$ | Bu42 |
| | $^D$TGTGGGCA$_{3'}$ | DT40 |
| | $^D$L-TGTGGG$_{3'}$ | Bu30 |
| | $^D$L-TGTGGGCAAGTA$_{3'}$ (SEQ ID NO:7) | Bu50 |

$^5$CGTGCGGGTGCG$_S$ (SEQ ID NO:6)

DNA target  $_{3'}$TAGCACGCGCCACGC——ACACCCGTTCATT (SEQ ID NO:8)

RNA target  $_{3'}$UAGCACGCGCCACGC——ACACCCGUUCAUU (SEQ ID NO:9)

SEQUENCE LISTING

```
<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: chemically synthesized DNA
```

-continued

<400> SEQUENCE: 1
gtgggcaaga gt                                                              12

<210> SEQ ID NO 2
<211> LENGTH: 12
<212> TYPE: DNA
<213> ORGANISM: Artificial Sequence
<220> FEATURE:
<223> OTHER INFORMATION: chemically synthesized DNA

<400> SEQUENCE: 2
gugggcaaga gt                                                              12

<210> SEQ ID NO 3
<211> LENGTH: 13
<212> TYPE: DNA
<213> ORGANISM: Artificial Sequence
<220> FEATURE:
<223> OTHER INFORMATION: chemically synthesized DNA

<400> SEQUENCE: 3
tgugggcaag agt                                                             13

<210> SEQ ID NO 4
<211> LENGTH: 47
<212> TYPE: DNA
<213> ORGANISM: Artificial Sequence
<220> FEATURE:
<223> OTHER INFORMATION: chemically synthesized DNA

<400> SEQUENCE: 4
atattcgacc accaccgcg gccgccacac ccgttctcac gcgactg                         47

<210> SEQ ID NO 5
<211> LENGTH: 47
<212> TYPE: DNA
<213> ORGANISM: Artificial Sequence
<220> FEATURE:
<223> OTHER INFORMATION: chemically synthesized DNA

<400> SEQUENCE: 5
atattcgacc accaccgcg gccaccacac ccgttctcac gcgactg                         47

<210> SEQ ID NO 6
<211> LENGTH: 11
<212> TYPE: DNA
<213> ORGANISM: Artificial Sequence
<220> FEATURE:
<223> OTHER INFORMATION: chemically synthesized DNA

<400> SEQUENCE: 6
cgtgcggtgc g                                                               11

<210> SEQ ID NO 7
<211> LENGTH: 12
<212> TYPE: DNA
<213> ORGANISM: Artificial Sequence
<220> FEATURE:
<223> OTHER INFORMATION: chemically synthesized DNA

<400> SEQUENCE: 7
tgtgggcaag ta                                                              12

```
                         -continued

<210> SEQ ID NO 8
<211> LENGTH: 28
<212> TYPE: DNA
<213> ORGANISM: Artificial Sequence
<220> FEATURE:
<223> OTHER INFORMATION: chemically synthesized DNA

<400> SEQUENCE: 8
tagcacgcgc cacgcacacc cgttcatt                              28

<210> SEQ ID NO 9
<211> LENGTH: 28
<212> TYPE: RNA
<213> ORGANISM: Artificial Sequence
<220> FEATURE:
<223> OTHER INFORMATION: chemically synthesized RNA

<400> SEQUENCE: 9
uagcacgcgc cacgcacacc cguucauu                              28
```

US 7,745,614 B2

UNIVERSAL LINKER COMPOSITIONS FOR THE RELEASE OR TRANSFER OF CHEMICAL AGENTS FROM A POLYNUCLEOTIDE

FEDERALLY-SPONSORED RESEARCH OR DEVELOPMENT

This invention was made with Government support under contracts GM062658 awarded by the National Institutes of Health and DAAD19-03-1-066 awarded by the Department of the Army. The Government has certain rights in this invention.

This invention was made with Government support under contract GM068122 and DAAD19-03-1-0066 awarded by the National Institutes of Health and Army Research Office. The Government has certain rights in this invention.

BACKGROUND OF THE INVENTION

The detection of specific nucleic acid sequences is immensely useful in molecular medicine. The possibilities for useful detection and quantitation of specific genes and gene products are nearly endless. Genotyping methods are of interest for prenatal diagnosis; as well as detecting changes in genotype associated with disease, for example during oncogenesis. Genotyping methods also find use in pharmacogenomics, to determine an individual's profile for drug metabolism, including the likelihood of adverse reactions and responsiveness to treatment. Other important areas of research include analysis of mRNA for expression, alternative splicing and SNP variation. In addition to analysis of expression, and of sequence polymorphisms, there is significant interest in simply determining whether a target sequence is present in a sample, for example in the detection and identification of microbial species in clinical and environmental samples.

Fast, simple and accurate methods of detecting and analyzing the presence or absence of nucleic acids, which may differ by as little as one nucleotide from others, are of great interest. In some cases, the nucleic acids may be present in minute quantities or concentrations, which underscores the need for high sensitivity as well. Many methods of detecting the presence of nucleic acid sequences are known in the art, including Northern and Southern blots, microarray hybridization, and the like. These methods have typically relied on hybridization kinetics between the target and probe species, coupled with varying temperature and ionicity to provide specificity. However, there are some significant drawbacks to these methods in terms of specificity and sensitivity.

A number of laboratories have investigated the use of non-enzymatic fluorescence based approaches for RNA or DNA detection, relying on the formation of bonds, hybridization of fluorescent oligonucleotides, or changes in secondary structure to detect genetic sequences. For example, see Xu and Kool (1997) Tetrahedron Lett. 38:5595-5598; Paris et al. (1998) N.A.R. 26:3789-3793; Okamoto et al. (2003) JACS 125:9296-9297; Tyagi and Kramer (1996) Nat. Biotech. 14:303-308; Kuhn et al. (2001) Antisense Nucleic Acid Drug Dev. 11:265-270; and International Patent application WO 2004/010101. Also of interest are U.S. Pat. No. 5,571,903 (Gryaznov); and U.S. Pat. No. 4,958,013 (Letsinger).

Self-ligation reactions have been developed for sequence detection, where the chemistry for joining two short oligonucleotide probes is incorporated into the ends of the probe molecules themselves. Such self-ligation reactions can be highly selective for single nucleotide differences in the target molecule. See, for example, Xu and Kool (2000) JACS 122: 9040-9041; Xu et al., (2001) Nat. Biotech. 19:148-152; Ficht et al. (2004) JACS 126:9970-9981; and Gryaznov and Letsinger (1993) JACS 115:3808-3809. In a recent advance, the chemistry for ligation was activated by a group that acted both as leaving group and as fluorescence quencher, thus enabling the probes to become fluorescent in the presence of a complementary target (Sando and Kool (2002) J. Am. Chem. Soc. 124 (10): 2096-2097).

Previously described self-ligation reactions have also had some limitations, however. The rate of reaction can be significantly slower than enzymatic ligations. In addition, prior art methods have placed the DNA end activation directly on a terminal T nucleoside, which would require the synthesis of four different modified nucleosides for application to all sequences. Finally, ligation reactions typically yield only one signal per target molecule, because the ligation product is stably bound to the target, and therefore does not readily dissociate.

While nonenzymatic approaches can offer advantages in cost, simplicity, and in vivo utility, they have not thus far provided for appreciable amplification of signals, which is useful in detecting target sequences present at low concentrations or in low numbers. Structures of suitable probes that address this issue, and provide for simplified probe preparation, are described herein.

Other Publications

Strategies for using pairs of modified oligonucleotides to generate amplified products or signals have been described. Ma and Taylor, Proc. Natl. Acad. Sci. USA 2000, 97, 11159-11163; Ma and Taylor, Bioorg. Med. Chem. 2001, 9, 2501-2510; and Brunner et al., J. Am. Chem. Soc. 2003, 125, 12410-12411 have described the combination of a hydrolysis catalyst on one oligonucleotide with a leaving group (in the form of an ester) on the other, resulting in the release of multiple leaving groups for each targeted complementary strand of DNA. Those approaches have generated ca 3-35 turnovers. The former has reported the generation of fluorescence signals, albeit without the demonstration of turnover (Ma and Taylor, Bioconjugate Chem. 2003, 14, 679-683). None of these approaches rely on ligation.

Ligations of amino-conjugated oligonucleotides have been investigated by Luther et al., Nature 1998, 396, 245-248 and by Zhan and Lynn, J. Am. Chem. Soc. 1997, 119, 12420-12421. The former approach requires denaturation cycles for turnover. The latter strategy isothermally generates as much as >50 turnovers in ligation, but it requires a separate reagent (borohydride), and it is not clear how the approach could generate easily detectable signals, such as those provided by the present invention.

Ficht et al., supra. developed peptide nucleic acid (PNA) probes that ligate by native chemical ligation; such probes have not been demonstrated to undergo turnover, nor do they generate fluorescent signals. RNA-detecting ribozymes are well documented to undergo turnover (Wang and Sen, J. Mol. Biol. 2001, 310, 723-734; Komatsu et al., Biochemistry 2002, 41, 9090-9098); however, a recent example of a DNAzyme designed to generate fluorescence signals in detection of an RNA documented only 4 signals per target (Sando et al., J. Am. Chem. Soc. 2003, 125, 15720-15721).

SUMMARY OF THE INVENTION

Compositions of modified polynucleotide probes and linker reagents for their synthesis are provided. The polynucleotide probes are modified at the 5' terminus by a functional group, which is linked to the polynucleotide through an activating leaving group and a tether. "Functional groups", as defined herein, provide for detectable or functional changes following their release from the modified polynucleotide, and include drugs, prodrugs, fluorescence quenchers, fluorochromes, etc. Linker reagents for synthesis of the modified polynucleotides are simple and inexpensive to prepare, and they can be appended to any polynucleotide in automated steps on a standard DNA synthesizer.

In some methods of interest, the modified polynucleotide is reacted with a second polynucleotide, where the sequences of the first and second polynucleotide may hybridize to neighboring sites of a target sequence. The second polynucleotide usually comprises a nucleophile attached to the 3' hydroxyl, which can attack the electrophilic atom adjacent to the activating leaving group in a ligation or transfer reaction, thereby displacing the functional group.

In a ligation reaction between a pair of probes, the nucleophile displaces the leaving group on the tether, thereby linking the pair of probes through the tether and releasing the functional group. The tether is optionally of a composition that destabilizes hybridization between the ligation product and its complementary target sequence without destabilizing the transition state for ligation. The ligation product can be released from the target sequence if desired, and therefore the target sequence can be made available for additional rounds of probe binding and ligation.

Alternatively, in a transfer reaction between a pair of probes, the nucleophile displaces the functional group, which functional group is transferred to the second polynucleotide in the absence of a ligation between the two probes.

The probes are useful in a variety of reactions triggered by specific hybridization to a target nucleic acid. Depending on the nature of the functional group, reactions triggered by hybridization may result in drug release; release of a fluorescence quencher; release of a fluorescent tag; chemical ligation; transfer of a quencher or fluorescent tag; and the like. The compositions and methods can be used in both in vitro and in vivo applications.

In one embodiment of the invention, a universal linker reagent is provided, which can be reacted with any polynucleotide sequence to provide a modified polynucleotide of the invention, conveniently during synthesis. Such linker reagents may be provided with a suitable functional group, or may be provided as a linker reagent to which the functional group is added during a subsequent synthesis reaction. The linker can be added to any polynucleotide using conventional solid state oligonucleotide synthesis reactions, for example in an automated synthesizer using phosphoroamidite or H-phosphonate chemistry.

In a related embodiment, a modified polynucleotide is provided, where the polynucleotide comprises a 5' functional group linked through an electrophile and a tether. In addition to the functional group, the polynucleotide and/or the nucleophilic polynucleotide may further comprise a fluorescent tag. The modified polynucleotides may be provided as a single species, in pairs as described above, or as a plurality of species and/or pairs. The modified polynucleotides or universal linker may be provided in solution; in a purified form, e.g. lyophilized; bound to a solid support, such as beads, arrays, and the like.

In another embodiment, methods are provided for the specific detection of polynucleotides, including mRNA, genomic DNA, extrachromosomal DNA, rRNA, etc., in a variety of platforms. Samples suitable for analysis include isolated polynucleotides; cell lysates; whole cells and tissues, which may be live or fixed; and whole organisms. Kits for practice of the methods are also provided.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 1A-1B. Structures and sequences studied. A. Structures and ligation mechanism of three new dabsyl-quenched universal linkers reported herein, compared with the previous Dabsyl-dT for self-ligating DNA probes. B. DNA sequences tested for ligation reactions. Thio1-Thio3 are nucleophilic probes containing 3'-phosphorothioate groups (denoted by subscript "s"). "flu" denotes fluorescein-conjugated T.

FIG. 2A-2D. Effect of linker structures and sequences on ligation rates, as measured by fluorescence intensity over time. (A) Comparison of electrophilic linkers DEt, DPr and DBu with previous dabsyl-T (DT) strategy. (B) Rates of bulged nucleotide strategies (see FIG. 1). (C) Effect of nucleophile location on rates of DPr linker ligations. The Dabsyl-T (DT) case is shown for comparison. (D) Effects of single-base mismatches on relative ligation rates for DPr and DBu universal linkers. The reactions were done under the following conditions; dabsyl probe (100 nM), phosphorothioate (100 nM), target DNA (100 nM) in pH 7.0 PIPES buffer (70 mM) containing $MgCl_2$ (10 mM) at 25° C.

FIG. 3. Probe and target sequences studied for turnover experiments. Thio5 and Thio6 are short and longer variants of Thio4. $^DL$ refers to the dabsyl-conjugated butanediol universal linker.

DETAILED DESCRIPTION OF THE INVENTION

Figure 4:
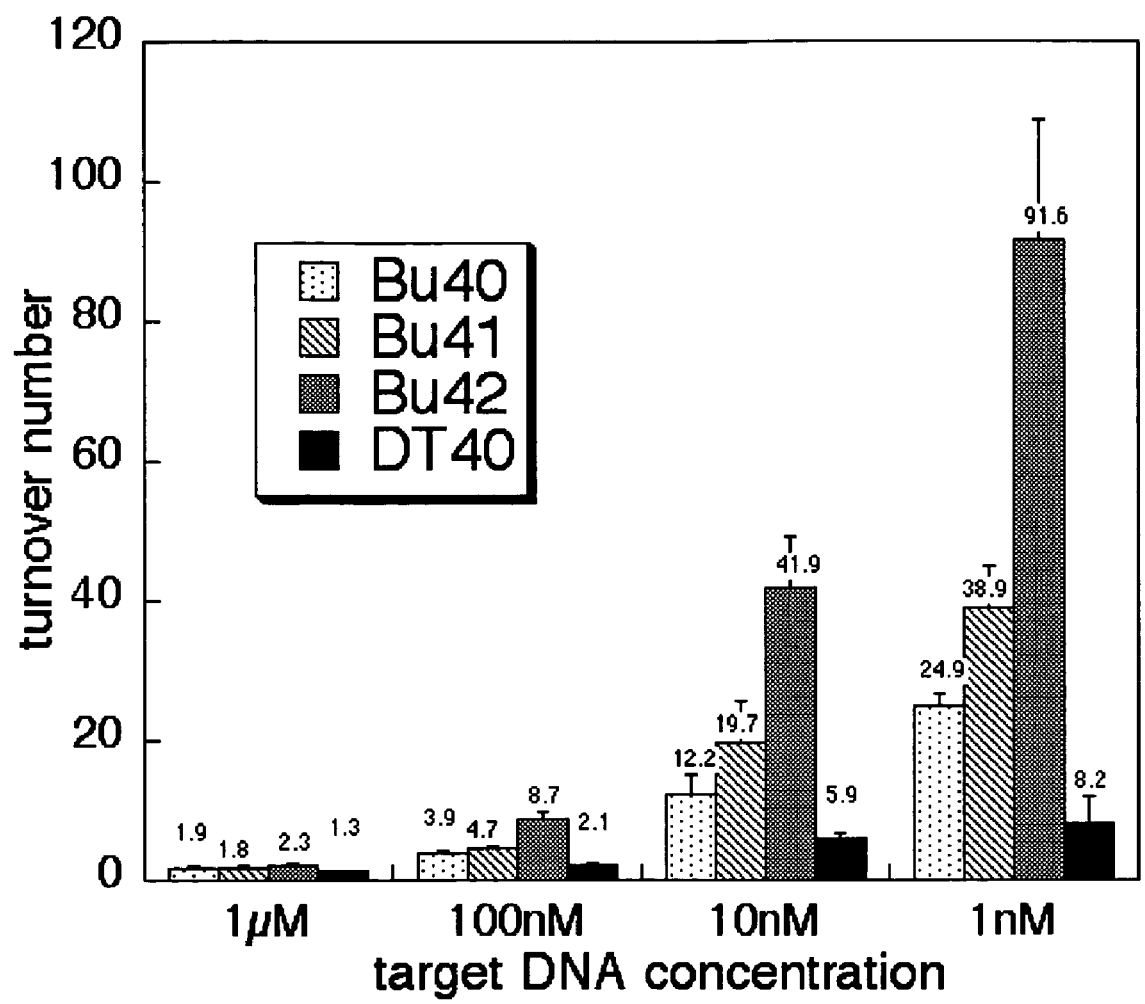
FIG. 4. Effect of target DNA concentration on turnover for four electrophilic probe designs. Turnover is given as equivalents of radioactive signal per mole of target DNA. The concentration of target DNA was varied at 1000 nM, 100 nM, 10 nM and 1 nM respectively in a pH 7.0 buffer (70 mM Tris-borate buffer) containing 10 μM dabsyl probe (Bu40, Bu41, Bu42 or DT40), 10 μM phosphorothioate probe (thio4) and 10 mM $MgCl_2$ at 25° C. Reactions were analyzed by 20% polyacrylamide gel electrophoresis after 24 h. Reactions were run at least three times and the data averaged; error bars show standard deviations.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Compositions

Compositions are provided for the preparation of modified polynucleotide probes. The polynucleotides are modified by reaction with a universal linker reagent of the invention. The modified polynucleotide comprises a functional group linked through an activating leaving group and a tether, usually to the 5' terminus. Conveniently, the universal linker is used to introduce the modification to the polynucleotide during in vitro non-enzymatic oligonucleotide synthesis, e.g. phosphoroamidite; H-phosphonate; etc., although for some purposes the modification may be introduced post-synthetically or during enzymatic synthesis, such as PCR, etc.

Universal linker reagents for preparing polynucleotides useful in ligation reactions have the following general structure:

Z-L-T-X                    I and a universal linker reagent for preparing polynucleotides useful in transfer reactions has the general structure:

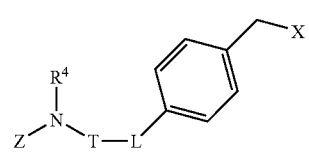

II wherein for structures I and II:
   Z is a functional group;
   L is an activating leaving group;
   T is a tether;
   X is phosphoroamidite or H-phosphonate; and
   $R^4$, where present, is a lower alkyl, i.e. of from 1 to 6 carbon atoms, which may be straight or branched, e.g., methyl, ethyl, n-propyl, 1-methylethyl (iso-propyl), n-butyl, n-pentyl, 1,1-dimethylethyl (t-butyl), and the like.

Modified polynucleotides for ligation reactions have the following general structure:

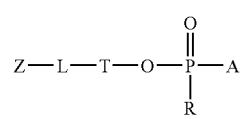

III and modified polynucleotides for transfer reactions have the following general structure:

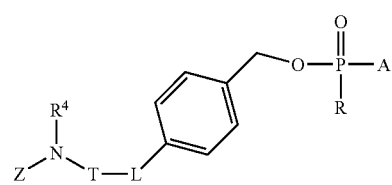

IV wherein for structures III and IV, Z, L, T, and $R^4$ are as described above; where A is any nucleotide or part of a polynucleotide, usually the 5' terminus of a polynucleotide; and
   R is $OR^1$; $O^-$; or a lower alkyl, which may be linear or branched; and $R^1$ is methyl or other lower alkyl, straight or branched; or β-cyanoethyl.

Collectively the modified polynucleotides of structure III and IV may be referred to as electrophilic probes, or separately referred to as an electrophilic ligation probe or electrophilic transfer probe, respectively.

Where it is present, X has the general structure known in the art for such in vitro oligonucleotide synthesis reagents, e.g. H-phosphonate; phosphoroamidite; etc. Descriptions of such reagents may be found, for example, in U.S. Pat. No. 4,458,066; Caruthers and Matteucci; Garegg et al. (1986) Tet. Lett. 27:4051-4054; Froehler and Matteucci (1986) Tet. Lett. 27:469-472; each herein specifically incorporated by reference.

Where X is phosphoroamidite, it will have the structure:

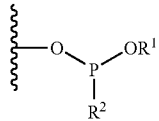
V where $R^1$ is a protecting group as known in the art, usually methyl or other lower alkyl, or β-cyanoethyl; and $R^2$ is a substituted primary amine or a secondary amine; including, without limitation, a primary or secondary amine substituted with one or two lower alkyls such as methyl, propyl, isopropyl, butyl, etc., including $N((CH(CH_3)_2)_2)$; $N(CH_3)_2$ $N(CH_2CH_3)_2$; tetrazole, imidazoles, cyclic amines, and the like.

In one embodiment of the invention, X has the structure:

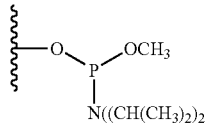
VI

Where X is an H-phosphonyl it will have the structure:

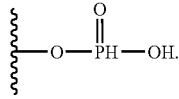
VII

The tether, T, is a chain of from about 2 to about 20 methylene groups in length, for example from about 2, 3, 4, 5, 6, 8, 10, 12, 14, 16, 18 or 20, where the methylene backbone is optionally substituted with a sulfur, nitrogen or oxygen heteroatom, which tether may comprise one, two, three, five, seven or more backbone heteroatoms. The bonds between methylenes may be saturated or unsaturated, usually not more than one, two, or three unsaturated bonds will be present in a tether backbone. Each of the backbone atoms may be substituted or unsubstituted, for example with an alkyl, aryl or alkenyl group. T includes, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like.

Some specific examples of T include:

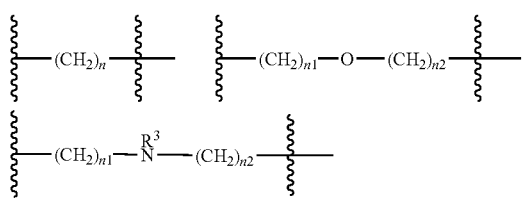
VIII

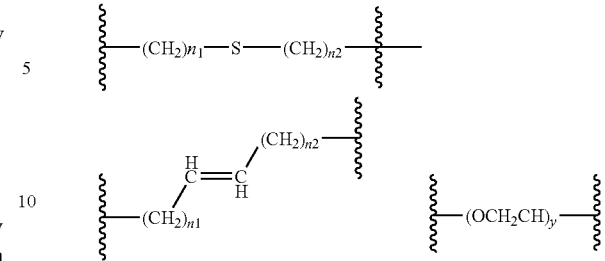

where n is from 2 to 20; and $n_1$ and $n_2$ are independently selected to be from 1 to 20; $n_1+n_2$ are usually not more than about 20; and y is from 1 to 7. The alkyl or alkenyl is optionally substituted, which substituent may include, without limitation, an alkyl, aryl, alkenyl, aralkyl, aralkenyl, cycloalkyl, cycloalkylalkyl or cycloalkylalkenyl group. It will be understood that substitution can occur on any carbon of the alkyl or alkenyl group.

$R^3$ is selected from an alkyl, usually branched or linear lower alkyl; hydroxy, alkoxy, aryloxy, haloalkoxy, cyano, nitro, mercapto, alkylthio, $-S(O)_pR^6$ (where p is 0 to 2), $-S(O)_pN(R^6)_2$ (where p is 0 to 2); $-OR^6$, $-C(O)OR^6$, $-C(O)N(R^6)_2$, $-N(R^6)_2$, $-N(R^6)C(O)OR^7$, $-N(R^8)C(O)R^8$, and $-R^8-N=N-O-R^7$; where each $R^6$, $R^7$ or $R^8$ is independently selected from the group consisting of hydrogen, alkyl, alkenyl, haloalkyl, haloalkenyl, aryl, aralkyl, aralkenyl, cycloalkyl, cycloalkylalkyl and cycloalkylalkenyl;

L, the activating leaving group, activates an adjacent atom for attack by a nucleophile. Such groups are known in the art. Specific non-limiting examples include sulfonates, carbonyl esters, para nitrophenyl esters, nitrophenyl esters, trifluoroacetyl esters, halogens, i.e. Cl, Br, I, F; nosylate, brosylate, tosylate, perchlorate, triflate, mesylate; and the like. In some instances, L is provided by the functional group Z.

The functional group, Z, may be absent or present. Where present, Z provides for a detectable or functional change in the modified polynucleotide upon displacement of the leaving group by ligation or transfer, and may include, without limitation, fluorophores, quenchers, drugs and prodrugs. Certain functional groups of interest provide both Z and L, e.g. DABSYL.

In one embodiment of the invention, Z is a quenching group, or quencher, where "quenching group" refers to any fluorescence-modifying group that can alter at least partly the light emitted by a fluorescent group. A polynucleotide having a quencher as Z will frequently also comprise one or more donor fluorophores. A fluorophore-quencher pair comprises two molecules having overlapping spectra, where the fluorophore emission overlaps the acceptor absorption, so that there is energy transfer between the excited fluorophore and the other member of the pair. It is not essential that the excited molecule actually fluoresce, it being sufficient that energy transfer can occur between the two.

Any fluorescence quencher can be used as Z. The quencher can be a DABSYL (dimethylamino-azobenzene-sulfonyl) group, DANSYL (5-dimethylaminonaphthalenesulfonyl); DIMAPDABSYL ((p-dimethylamino-phenylazo) azobenzenesulfonyl), other azobenzene-sulfonyl groups, benzenesulfonyl groups, or arenesulfonyl groups, any of which may comprise substituents such as amino, dialkylamino, nitro, fluoro, and cyano groups; anthraquinone, nitrothiazole, and nitroimidazole compounds; rhodamine dyes (e.g., tetramethyl-6-carboxyrhodamine (TAMRA); ROX; cyanine; coumarin; BODIPY dyes; fluorescein dyes; ALEXA dyes; and the like.

Where the functional group is a quencher, the modified polynucleotide may further comprise one or more donor or acceptor fluorophore(s), which is quenched prior to the release of the quencher. Any known method of incorporating a fluorophore into a nucleic acid molecule can be used. It is preferred that a fluorophore be located close to the quencher, but this is not required. The fluorophore can generally be located at any distance from the quencher sufficient to permit detection of ligation by monitoring the change in fluorescent properties. For example, the fluorophore can be located 1, 2, 3 or more, and usually will be not more than about 10, 15 or 20 nucleotides away from the quencher.

The covalent attachment of dyes to nucleic acids can be achieved by a variety of methods known to those of skill in the art. The covalent attachment of dyes to nucleic acids is reviewed in Davies et al. (2000) Chem. Soc. Rev. 29:97-107, which is incorporated herein by reference in its entirety. Examples include, but are not limited to: incorporation of the dyes during the synthesis of nucleic acids, typically solid phase synthesis, post-synthetic labeling of either synthetic nucleic acids or nucleic acids derived through enzymatic reactions, e.g. the PCR reaction, replacement of a nucleotide with a fluorescence modified nucleotide during in vitro synthesis; enzymatic methods of incorporation of dyes into nucleic acids, e.g. the use of dye conjugated deoxynucleotide triphosphates in primer elongation reactions such as a PCR reaction; and the like.

The efficiency of quenching (i.e. the unquenched fluorescence with the fluorescence quenching group absent divided by the quenched fluorescence with the fluorescence quenching group present) may be at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 200 fold, at least about 300 fold, at least about 400 fold, at least about 500 fold, at least about 600 fold, at least about 700 fold, at least about 800 fold, at least about 900 fold, at least about 1000 fold, at least about 2000 fold, at least about 3000 fold, at least about 4000 fold, or at least about 5000 fold.

In another embodiment, the functional group is a fluorescent or phosphorescent group, where "fluorescent group" or "fluorophore" refers to a molecule that, when excited with light having a selected wavelength, emits light of a different wavelength, which may emit light immediately or with a delay after excitation. Fluorophores, include, without limitation, fluorescein dyes, e.g., 5-carboxyfluorescein (5-FAM), 6-carboxyfluorescein (6-FAM), 2',4',1,4,-tetrachlorofluorescein (TET), 2',4', 5',7',1,4-hexachlorofluorescein (HEX), and 2',7'-dimethoxy-4',5'-dichloro-6-carboxyfluorescein (JOE); cyanine dyes, e.g. Cy3, CY5, Cy5.5, etc.; dansyl derivatives; 6-carboxytetramethylrhodamine (TAMRA), BODIPY fluorophores, tetrapropano-6-carboxyrhodamine (ROX), ALEXA dyes, Oregon Green, and the like.

Combinations of fluorophores also find use, e.g. where transfer or release of a fluorophore leads to a color change. Various combinations are of interest, including a fluorophore that is present on the nucleophile probe in combination with a fluorophore on the electrophile probe, where the fluorophores may be the same or different. A quencher may be included in combination with two or more fluorophores. For example, an electrophile probe may comprise a quencher as Z and a covalently attached fluorophore; and a nucleophile probe may comprise a second fluorophore that, when in proximity of the first fluorophore, results in a color change.

In another embodiment, the functional group is a drug or prodrug, which may include chemotherapeutic agents for neoplastic tissues, anti-inflammatory agents for ischemic or inflamed tissues, hormones or hormone antagonists for endocrine tissues, ion channel modifiers for cardiovascular or other tissues, and neuroactive agents for the central nervous system. Exemplary of pharmaceutical agents suitable for this invention are those described in The Pharmacological Basis of Therapeutics, Goodman and Gilman, McGraw-Hill, New York, N.Y., (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

A "chemotherapeutic agent" is a chemical compound useful in the treatment of cancer. Examples of chemotherapeutic agents include adriamycin, doxorubicin, 5-fluorouracil (5-FU), cytosine arabinoside (ARA-C), cyclophosphamide, thiotepa, busulfan, cytoxin, taxol, methotrexate, cisplatin, melphalan, vinblastine, bleomycin, etoposide, ifosfamide, mitomycin c, mitoxantrone, vincristine, VP-16, vinorelbine, carboplatin, teniposide, daunomycin, carminomycin, aminopterin, dactinomycin, mitomycins, nicotinamide, esperamicins, melphalan and other related nitrogen mustards, and endocrine therapies (such as diethylstilbestrol (des), tamoxifen, LHRH antagonizing drugs, progestins, anti-progestins, etc). One chemotherapeutic drug of interest is a methotrexate sulfonate analog.

In one embodiment of the invention, the functional group is a prodrug. The term "prodrug" refers to a precursor or derivative form of a pharmaceutically active substance that is less active than the parent drug and is capable of being converted into the more active parent form. Use of prodrugs allows the modulation of onset and/or duration of action of a biologically-active compound in vivo. A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

Prodrugs of interest include, but are not limited to, phosphate-containing prodrugs, thiophosphate-containing prodrugs, sulfate-containing prodrugs, peptide-containing prodrugs, D-amino acid-modified prodrugs, glycosylated prodrugs, P-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Glucuronide prodrugs can be enzymatically converted to active agents by beta-glucuronidase. Other prodrugs are based on ester or phosphate linkages have been reported.

In some methods of the invention, a pair or plurality of polynucleotide probes is used. A first modified polynucleotide probe comprises the functional group, activating group and tether; while a second or additional polynucleotide probe comprises a nucleophile, usually a 3' nucleophile, which reacts with the electrophilic probe in a ligation or transfer reaction, and may be referred to as a nucleophilic probe. In general, nucleophilic groups of the invention may include, without limitation, phosphorothioate and phosphoroselenoate groups, thiol and thiolate groups, hydroxy and oxyanion groups, amines, hydroxylamines, hydrazines, hydrazides, phosphines, thioacids and their conjugate bases, selenols and selenoates. The nucleophile is readily added to an oligonucleotide, for example a commercially available phosphorylation reagent; and sulfurizing agent can be used to provide a phosphorothioate group. The nucleophilic probe may further comprise fluorophore(s) and/or fluorescence quenchers.

When the nucleophilic probe and the electrophilic probe are brought into close proximity, e.g. by hybridizing to neighboring sequences on a target polynucleotide, the nucleophilic probe reacts with the tether on the electrophilic probe to release or transfer the functional group. The term "proximity" refers to the relative positions of the electrophile and nucleophile, and occurs when the two groups are sufficiently close to react.

Reference may be made herein to the hybridization, or potential for hybridization, of probe sequences to a target sequence. For example, the polynucleotide portion of a first and second probe may hybridize, respectively, to "neighboring" sites on the target through base complementarity. Two such sites, when aligned on the target polynucleotide sequence, are considered to be "neighboring" if the sites are contiguous on the target; are separated by one, two, three or more bases on the target; or overlap by one, two three or more bases on the target.

Oligonucleotide, or polynucleotide means either DNA, RNA, single-stranded or double-stranded, and derivatives thereof, including, but are not limited to: 2'-position sugar modifications; propynyl additions, for example at the at the 5 position of pyrimidines; 5-position pyrimidine modifications, 7- or 8-position purine modifications, modifications at exocyclic amines, 5-methyl cytosine; 5 bromo-cytosine; alkynyl uridine and cytosine; substitution of 4-thiouridine, substitution of 5-bromo or 5-iodo-uracil; backbone modifications, including peptide nucleic acids (PNA), locked nucleic acids (LNA), etc., methylations, morpholino derivatives; phosphoroamidate derivatives; unusual base-pairing combinations such as the isobases isocytidine and isoguanidine and the like. Derivatives can also include 3' and 5' modifications such as capping.

The polynucleotide can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Modifications to introduce a universal primer of the invention may be performed post-synthetically; or a modified polynucleotide may be used as a primer in a synthetic reaction, e.g. PCR; and the like.

As is used in the art, the term "oligonucleotide" usually refers to shorter molecules, usually of at least about 3 bases in length, more usually at least 4, 5, or 6 bases; for many embodiments of the invention, preferred oligonucleotides are at least 7 bases, at least 8 bases, at least 10 bases, at least 12 bases, and not more than about 100 bases in length, usually not more than about 50 bases in length, or any length range between any two of these lengths. The term "polynucleotide" may refer to any length of nucleic acid greater than a single base; although in many instances will be used to refer to molecules as present in living organisms, which range from about 50 bases in length to many megabases, in the case of genomic DNAs. It will be understood by those of skill in the art that the linkers described herein are readily attached to any polynucleotide. For many assays of interest, one probe, which may be the electrophilic probe or the nucleophilic probe, will be of a length that is sensitive to small differences in sequence.

Modified oligonucleotides of the invention may be provided in solution, or bound to a substrate. One, a pair or a plurality of modified probes may be provided in any configuration, although on a solid support it will be more usual for one member of a pair to be present on the support, and a second member to be provided in solution.

By "solid substrate" or "solid support" is meant any surface to which the probes of the invention are attached. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polystyrene and sulfonated polystyrene-divinyl benzene, quaternized product of chloromethylated polystyrene-divinyl benzene, PEG-polystyrene, PEG, polycarbonate, and blends thereof, and the like; metals, e.g. gold, platinum, silver, and the like; etc. The substrates can take a variety of configurations, including planar surfaces, filters, fibers, membranes, beads, particles, dipsticks, sheets, rods, etc.

In one embodiment, the substrate comprises a planar surface, and probes are attached to the surface. The probes may be attached in a uniform pattern or in an array in a plurality of probe spots. The density of labeled probes on the substrate will be such that a signal from the label can be detected. As such, the density will vary depending on the identity of the particular label. Where the probes are spotted on the array, the spots can be arranged in any convenient pattern across or over the surface of the support, such as in rows and columns so as to form a grid, in a circular pattern, and the like, where generally the pattern of spots will be present in the form of a grid across the surface of the solid support. The total number of probe spots on the substrate will vary depending on the concentration of binding member-complementing domain conjugates, as well as the number of control spots, calibrating spots and the like, as may be desired. In an alternative method, where the probes are not bound to a solid support, the assays of the invention may utilize such reaction vessels as 96 well plates, etc., as are known in the art.

In another embodiment, the substrate is a collection of physically discrete solid substrates, e.g. a collection of beads, individual strands of fiber optic cable, and the like. Each discrete substrate can have probes distributed across the surface or attached in one or more probe spots on the substrate. The collection of physically separable discrete substrates may be arranged in a predetermined pattern or may be separated in a series of physically discrete containers (e.g., wells of a multi-well plate).

The substrates can be prepared using any convenient means. One means of preparing the supports is to synthesize the probes, and then deposit them on the support surface. The probes can be deposited on the support using any convenient methodology, including manual techniques, e.g. by micropipette, ink jet, pins, etc., and automated protocols. The probes may also be covalently attached to the substrate, using methods known in the art. Alternatively, the probes can be synthesized on the substrate using standard techniques known in the art.

LIGATION REACTIONS

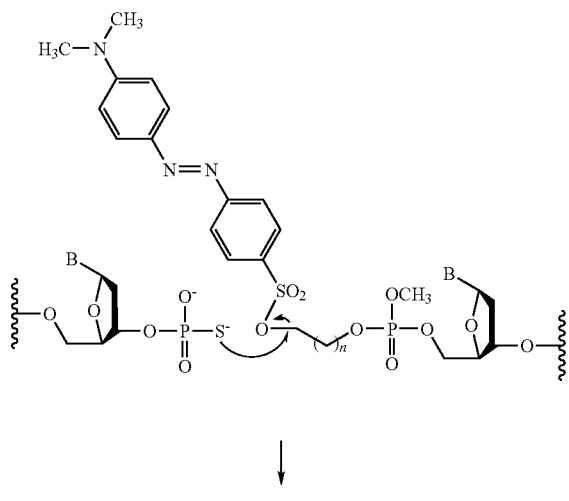

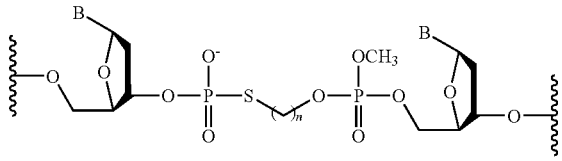

The above scheme shows an example of a ligation between a polynucleotide comprising a 3' phosphorothioate as a nucleophile, and the tether on a modified polynucleotide. The modified polynucleotide corresponds to previously described structure III, where Z is DABSYL; L (which is provided by the DABSYL group) is a sulfonate group; and T is an alkyl of length n. The reaction has been shown to proceed under a variety of conditions (see examples) and also including physiological conditions, as are found in vivo.

The electrophile is positioned at the end of a hydrocarbon tether, which is in turn linked to the 5' end of the probe via (in this example) phosphoramidite chemistry. After ligation of the nucleophilic probe to the tether, the product contains a flexible tether interrupting the two complementary half-segments that are complementary to neighboring positions on the target. Because of the length and flexibility of the tether, the ligation product is less favorable entropically than a similar product having a direct phosphodiester linkage. If desired, the ligation product of the invention can dissociate, even under isothermal conditions, allowing a new pair of probes to bind, generating multiple signals per target.

TRANSFER REACTIONS

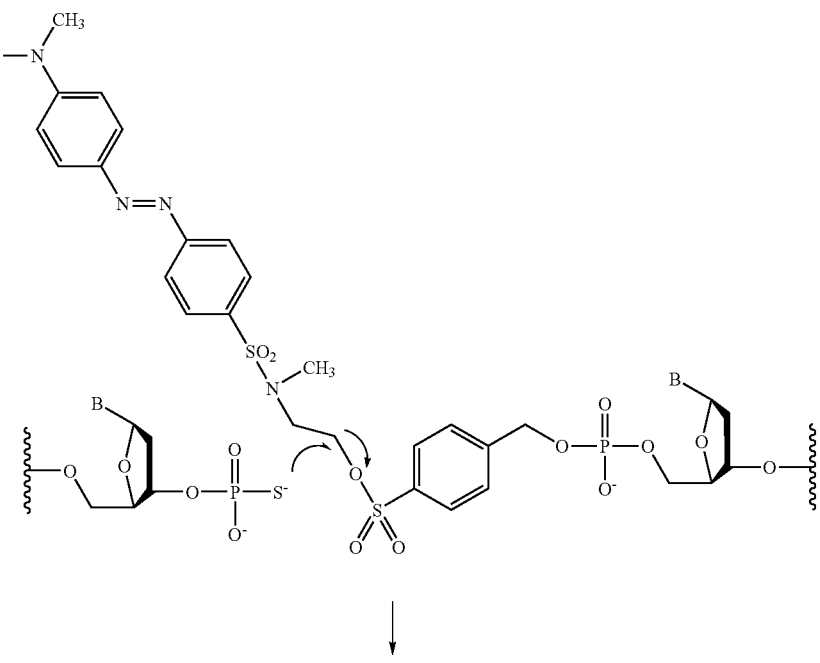

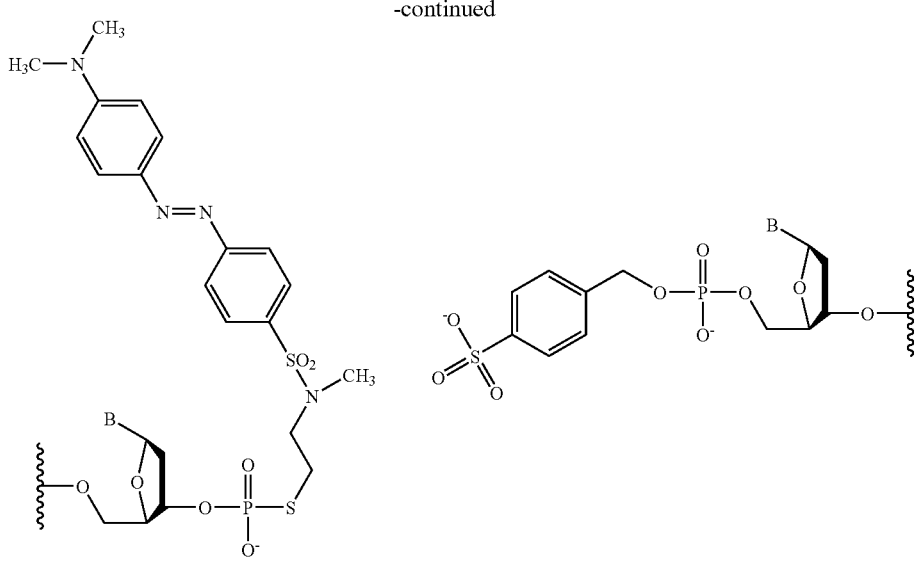

The above reaction scheme shows an example of a transfer between a polynucleotide comprising a 3' phosphorothioate as a nucleophile, and the tether on a modified polynucleotide. The modified polynucleotide corresponds to previously described structure IV, where Z is DABSYL; L is a sulfonate group; and T is an alkyl of length n=2.

In this example, Z is a quencher, which can be transferred away from a first probe comprising a fluorophore, resulting in increased fluorescence upon transfer. Where the second probe comprises a fluorophore, there will be a decrease in fluorescence as a result of the transfer. Alternatively, Z may be a fluorophore, which is transferred from a first probe to a second probe, for example where one of the probes is bound to a solid substrate; or the like. As with the ligation reaction, the reaction product can be made to dissociate even under isothermal conditions, allowing a new pair of probes to bind, generating multiple signals per target.

Synthetic Methods

A modified polynucleotide is generated by reacting a universal linker with a polynucleotide of desired length and sequence. Conveniently, the modification is performed in solid phase following synthesis of an oligonucleotide, using readily available reagents and equipment (see, for example, U.S. Pat. No. 4,458,066; or a review of the art in "Perspectives in Nucleoside and Nucleic Acid Chemistry"; ISBN: 3-90639-021-7, herein incorporated by reference).

In a phosphoramidite method, a series of deprotection, coupling, capping, and oxidation steps is repeated until the nucleotide chain of interest is formed. The strand is formed 3' to 5'. The first step requires a column that has a protected form of the terminal (3') monomer chemically bound to its matrix. The nascent oligonucleotide chain will stay attached to this support as each activated monomer is linked to its 3' neighbor. In DNA synthesis, the protected monomers are deoxyribonucleoside 3-phosphoramidites containing dimethoxytrityl (DMT) blocking groups on the 5'-oxygen atoms. These monomers are activated by treatment with a weak acid prior to chain elongation. Deprotection is the first step of each chain elongation cycle. An acid wash removes the DMT blocking group from the terminal monomer. After deprotection, the terminal monomer has a ready-to-react hydroxyl group (OH) at its 5' end. The second step is coupling. Because phosphoramidites react with water, coupling is carried out under anhydrous conditions. In this step, the next activated monomer in the sequence is added to the vessel. The 5'-OH ends of unreacted terminal monomers are blocked via acetylation. In the fourth step, the phosphite triester is oxidized to the more stable phosphotriester linkage. This cycle is repeated for each added monomer.

In an H-phosphonate method, the monomer that is able to be activated is usually a 5'-DMT-base-protected, nucleoside 3'-hydrogen phosphonate. The presence of the H-phosphonate moiety on these monomers renders phosphate protection unnecessary. The same base protecting groups are used in phosphite triester chemistry. There are four steps to the synthesis of an oligonucleotide using H-phosphonate chemistry. In a first step the 5' protecting group is removed by exposure to trichloroacetic acid and in dichloromethane. In coupling, the monomer is activated by a hindered acyl chloride, the resultant anhydride reacts with a free oligonucleotide 5'-OH end, forming an H-phosphonate analog of the internucleotidic linkage. Capping is achieved using the TEA salt of isopropyl phosphite. After synthesis of the entire sequence is complete, all of the H-phosphonate bonds are simultaneously oxidized to phosphodiester linkages. Through alternate oxidation steps, H-phosphonate oligonucleotides can be converted to phosphorothioates, phosphorotriesters and various other analogs.

Where it is desired, one or more fluorescent group(s) can be added as a modified phosphoroamidite or H-phosphonate reagent, usually from between about 1 to 20 nucleotides before the 5' terminus.

When the oligonucleotide has reached the desired length, the final cycle is used to add a universal linker, which optionally includes the releasing group of interest. Linkers may be synthesized as described in the Examples. The linker is usually reacted using the same reagents as the oligonucleotide synthesis reactions, as known to those of skill in the art.

The completed modified oligonucleotide is then cleaved from the support and deprotected by treatment, e.g. with concentrated ammonium hydroxide, usually with a milder deprotection treatment using methods known in the art, e.g.

potassium carbonate/methanol. A subsequent heat treatment removes the remaining protecting groups. The final product may purified by chromatography or electrophoresis, including ion exchange, HPLC, PAGE, etc. In some cases, crude oligonucleotides can be precipitated, or passed over a desalting column, and used without further purification.

In an alternative composition, the Z group is not specified by the linker reagent, but is added in a synthetic reaction. The unspecified linker has the structure:

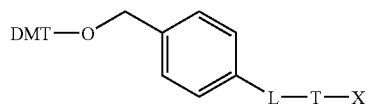

IX

Where L; T and X are as previously defined for structures I-IV. Following or during addition of the linker to the oligonucleotide, the functional group Z is added. Removal of DMT and addition of the Z group is performed using standard phosphoroamidite chemistry steps.

Diagnostic Methods

The present invention includes methods for the detection or quantification of a nucleic acid target sequence, comprising the steps of: contacting a sample suspected of containing the target sequence with a first polynucleotide probe, wherein said polynucleotide probe is modified with a universal linker and functional group as described herein; and a second, nucleophilic oligonucleotide probe, wherein the first and second probes may hybridize to neighboring sequences on a target nucleic acid under conditions permissive for the release of Z from the first probe; and measuring the change in fluorescence of the sample, where the level of change is proportional to the amount of target sequence present in the sample. The presence of the tether provides for improved reaction speed, and for amplification if desired of the signal, through repeated rounds of ligation or transfer.

Where Z is a quencher, the intensity or wavelength of emission will change, for example by release or transfer of the quencher away from a fluorophore. Where Z is a fluorophore, the level of fluorescence can increase, decrease, or change color. For example a first probe may bound to a substrate, where the fluorescent group Z is released from the substrate by the reaction with the second polynucleotide. Alternatively, in a transfer reaction, a fluorescent group may be transferred to a probe that is bound to a substrate, which fluorescence may then be quantitated after washing unbound material from the substrate.

The sequence of the probe(s) is selected to be complementary, competitive, mismatched, etc. with respect to a target sequence, as dictated by the specific interests of the method. In some embodiments, the probe sequences are chosen to be sufficiently selective that there is a detectable difference between binding to a perfect match at the target, and to a single nucleotide mismatch at the target. A highly selective probe binds with high preference to the exact complementary sequence on a target strand as compared to a sequence that has one or more mismatched bases. Less selective probes are also of interest for some embodiments, where hybridization is sufficient for detectable reactions to occur in the presence of one, two three or more mismatches, where a mismatch may include substitutions, deletions, additions, etc.

A "target sequence" refers to the particular nucleotide sequence of the target polynucleotide, which may be hybridized by a probe or probes. Exemplary targets include viral polynucleotides, bacterial polynucleotides (such as mRNA, rRNA), and eukaryotic rRNA, mRNA, genomic DNA, etc.

As used herein, a "test sample" is a sample suspected of containing nucleic acids to be analyzed for the presence or amount of an analyte polynucleotide. Nucleic acids of the test sample may be of any biological origin, including any tissue or polynucleotide-containing material obtained from a human. For example, the nucleic acids of the test sample may be from a biological sample that may include one or more of: tissue or organ lavage, sputum, peripheral blood, plasma, serum, bone marrow, biopsy tissue including lymph nodes, respiratory tissue or exudates, gastrointestinal tissue, cervical swab samples, semen or other body fluids, tissues or materials. Biological samples may be treated to disrupt tissue or cell structure, thereby releasing intracellular components into a solution which may contain enzymes, buffers, salts, detergents and the like. Alternative sources of nucleic acids may include water or food samples that are to be tested for the presence of a particular analyte polynucleotide that would indicate the presence of a microorganism.

Applications for such methods include in vitro diagnostics, including clinical diagnostics, research in the fields of molecular biology, high throughput drug screening, veterinary diagnostics, agricultural-genetics testing, environmental testing, food testing, industrial process monitoring, etc. In vitro diagnostics and clinical diagnostics relate to the analysis of nucleic acid samples drawn from the body to detect the existence of a disease or condition, its stage of development and/or severity, and the patient's response to treatment. In high throughput drug screening and development, nucleic acids are used to analyze the response of biological systems upon exposure to libraries of compounds in a high sample number setting to identify drug leads. Veterinary diagnostics and agricultural genetics testing provide a means of quality control for agricultural genetic products and processes. In environmental testing, organisms and their toxins that characterize an environmental medium, e.g. soil, water, air, etc., are analyzed. Food testing includes the qualitative identification and/or quantitation of organisms, e.g. bacteria, fungi, etc., as a means of quality control.

In such assays, a change in fluorescent signal is generated upon the presence of a complementary nucleic acid sequence in the analyte. The fluorescent signal is monitored and quantified with fluorescence detectors, such as fluorescence spectrophotometers, microplate readers, UV lamps, PCR, commercial systems that allow the monitoring of fluorescence in real time reactions, or, in some instances, by the human eye.

In one embodiment, a homogeneous assay is conducted. In this embodiment of the invention, the nucleic acid probes hybridize with a complementary nucleic acid sequence, if present in the target, to release the Z group and effect a change in fluorescence. With appropriate target standards and concentration versus signal standard curves the method can easily be used to quantitate the target. In addition to single stranded target nucleic acids, double stranded target nucleic acids can also be detected by the nucleic acid probe following denaturation. Targets that can be specifically detected and/or quantified with this method include, but are not limited to, plasmid DNA, cloning inserts in plasmid DNA, mRNA transcripts, ribosomal RNA, PCR amplicons, restriction fragments, synthetic oligonucleotides, as well as any other nucleic acids and oligonucleotides.

In another embodiment, a plurality of probes is employed in assays to detect or quantify one or more nucleic acid targets, which assays may be performed in solution; in cells; on a solid substrate; etc. At least one nucleophile probe and at least one electrophile probe will be present; the selection of which probe comprises an electrophile and which comprises a nucleophile will be dictated by the specific requirements of the assay. Various formats may be used in such assays. The composition of fluorophores and/or quenchers will be selected to provide the desired information, including the use of multiple fluorophores with distinguishable signals.

For example, multiplex assays may be performed to simultaneously assay for a plurality of targets. A single probe species comprising an oligo-dT sequence can be used with a plurality of probe species in the simultaneous detection of multiple mRNA sequences. A plurality of nucleophile probes and a plurality of electrophile probes may be used to simultaneously assay for the presence of complementary target sequences.

Competition assays may also be performed. For example, a single nucleophilic probe complementary to a sequence of interest may be used with a plurality of electrophilic linker probes complementary to potentially variable neighboring sequences, e.g. polymorphic sequences, alternatively spliced sequences, etc. The probe having greatest complementarity can win the competition, yielding a fluorescence signal specific to that probe.

A fluorescent signal is generated, e.g. on a substrate comprising probes, upon the presence of a complementary nucleic acid sequence in the analyte; in solution; etc. The fluorescent signal that is generated in the assay can be monitored and quantified with fluorescence detectors, including fluorescence imagers, e.g. commercial instruments supplied by Hitachi Corp., San Bruno, Calif., fluorescence microscopes, confocal laser microscopes (confocal fluorescence scanners), e.g. commercial instruments from General Scanning, Inc., Watertown, Mass.

Assays based on detection of sequences present in individual cells may utilize fixed or living cells. Cells in a sample may be fixed, e.g. with 3% paraformaldehyde, and are usually permeabilized, e.g. with ice cold methanol; HEPES-buffered PBS containing 0.1% saponin, 3% BSA; covering for 2 min in acetone at −20° C.; and the like as known in the art. Living cells may also be assayed using the probes of the invention. Probes can be introduced into live cells using any one of many well-known methods for bringing oligonucleotides into cells, including electroporation, calcium phosphate transfection, ionic shock, microinjection, pore-forming peptides, uptake reagents, fusion of vesicles, etc. Many such reagents are commercially available. Such methods may utilize carrier molecules, including calcium-phosphate, DEAE dextran and cationic lipids. Nucleic acids can be adsorbed to unilamellar lipdsome vesicles comprising cationic lipids mixed with neutral lipids, which vesicles may be modified by the inclusion of various commercially available components, e.g. FuGENE 6; X-tremeGENE Q2; etc. (Roche Applied Science). Cationic polymers, including dendrimeric polyamines or homopolymers of positively charged amino acids such as poly-L-lysines, poly-D-lysines and poly-L-ornithines, HIV tat, Pseudomonas exotoxin, Drosophila Antennapedia and HSV-1 VP22 protein may also be used as carriers. Agents that enhance uptake may be covalently conjugated to the probes. Examples include cationic peptides, cholesterol, arginine-rich peptides, etc.

Flow cytometry is a convenient method to quantitate fluorescence signals from cells. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected fluorophores are capable of being read simultaneously, or in sequence during a single analysis, allowing of up to 5 or more fluorescent colors simultaneously. Readouts from such assays may be the mean fluorescence associated with individual fluorescent molecules, or the average fluorescence intensity, the median fluorescence intensity, the variance in fluorescence intensity, or some relationship among these.

Microscopic analysis of single cell multiparameter and multicell multiparameter multiplex assays are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

In a particular embodiment of the invention, RNA molecules from a biological source are detected and/or quantified. The RNA may be directly obtained from cells of interest; may be present in living or fixed cells; or may be converted to cDNA molecules and/or further amplified by PCR.

In many instances, such assays are conducted with mRNA samples obtained from a biological system under different environmental conditions, such as exposures to varying concentration of a drug candidate or mixtures of drug candidates, which can provide data on the efficacy, the safety profile, the mechanism of action and other properties of the drug candidates that are required in drug development. Alternatively, tissue samples may be probed for the presence of clinical conditions, e.g. the presence of pathogens; expression of tumor associated sequences; and the like.

In another embodiment of the invention, the probes are used to detect or quantify nucleic acid targets from genomic DNA, in order to analyze for the presence or absence of polymorphisms in the genomic DNA. The polymorphisms can be deletions, insertions, or base substitutions or other polymorphisms of the genomic DNA. Typically the polymorphisms are single nucleotide polymorphisms (SNPs), gene rearrangements, allelic variants; and the like.

Therapeutic Methods

Where Z is a drug or prodrug, the compositions of the invention find use in targeted drug delivery, where the drug or prodrug is released in the presence of the target nucleic acid, e.g. a pathogen sequence for the release of antimicrobial agents; the release of anti-inflammatory drugs in the presence of mRNA encoding cytokines or other molecules associated with inflammation; the release of cytotoxic agents in the presence of sequences associated with cancer; and the like.

In targeted drug delivery to an environment comprising a target nucleic acid sequence, the method comprises contacting a sample suspected of containing the target sequence with a first polynucleotide and a second polynucleotide probe of the invention, wherein Z is a drug or prodrug and wherein the first and second probes hybridize to adjacent, contiguous sequences on said target nucleic acid, under conditions permissive for the release of Z from said first polynucleotide, and the drug is selectively released into said environment in the presence of said target sequence.

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host. Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Kits

Also provided are kits for practicing the subject methods. The kits according to the present invention may comprise at least: one modified polynucleotide; and (b) instructions for using the provided modified oligonucleotide(s). Such modified polynucleotides may be provided lyophilized, in solution, or bound to a substrate. Kits may further include a second polynucleotide to form a pair that may hybridize to neighboring regions of a target sequence.

Kits may also be provided for use in the synthesis of oligonucleotides, comprising a universal linker; which is optionally loaded with a functional group; which may be provided with reagents for modifying a second polynucleotide probe, e.g. phosphorylating agents, etc. Such kits may also comprise modified H-phosphonate or phosphoroamidite derivatives, e.g. to introduce functional groups of interest into a modified polynucleotide.

The subject kits may further comprise additional reagents which are required for or convenient and/or desirable to include in the reaction mixture prepared during the subject methods, where such reagents include phosphoroamidite reagents and buffers for DNA synthesis; columns.

The various reagent components of the kits may be present in separate containers, or may all be precombined into a reagent mixture for combination with samples. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Materials and Methods
Synthesis of Dabsyl Linker Phosphoramidite Derivatives.

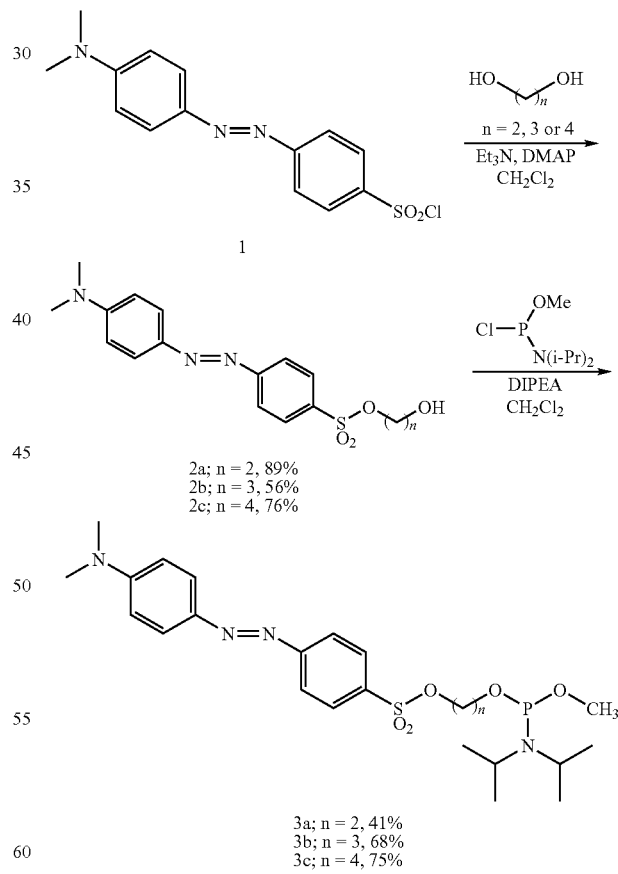

Compound 2a (ethylene linker). A solution of Dabsyl chloride (500 mg, 1.48 mmol), ethylene glycol (826 µL, 14.8 mmol), DMAP (50 mg, 0.4 mmol) and Et$_3$N (413 µL. 2.96 mmol) in CH$_2$Cl$_2$ (15 mL) was stirred for 1 hour and evaporated. The crude product was purified by column chromatography (SiO$_2$, CH$_2$Cl$_2$:AcOEt=5:1) to give 2a (462 mg, 89% as a yellow powder). $^1$H-NMR (CDCl$_3$, 500 MHz) δ=8.03-7.90 (m 6H, ArH (dabsyl)), 6.77 (m, 2H, ArH (dabsyl)), 4.20 (dd, 2H, H-1; J=4.5, 4.5 Hz), 3.84 (dt, 2H, H-2, J=4.5, 6.5 Hz), 3.14 (s, 6H, CH$_3$ (dabsyl), 2.35 (t, 1H, 2-OH, J=6.5 Hz); $^{13}$C-NMR (CDCl$_3$, 125 MHz) □=156.76, 153.55, 143.77, 134.89, 129.27, 126.22, 123.00, 111.72, 72.16, 60.94, 40.56; FABMS (NBA), m/e 349 [(M+H)$^+$]; HRMS calcd for C$_{16}$H$_{19}$O$_4$N$_3$PS [(M+H)$^+$] 349.1104, found 349.1096.

Compound 2b (propylene linker). Compound 2b was prepared from 1,3-propanediol (1.0 mL, 13.8 mmol) by the procedure for 2a. The crude product was purified by column chromatography (SiO$_2$, CH$_2$Cl$_2$:AcOEt=10:1) to give 2b (700 mg, 56% as a red powder). $^1$H-NMR (CDCl$_3$, 200 MHz) δ=7.97-7.81 (m 6H, ArH (dabsyl)), 6.70 (m, 2H, ArH (dabsyl)), 4.18 (t, 2H, H-1, J=6.2 Hz), 3.67 (dt, 2H, H-3, J=5.4, 5.4 Hz), 1.85 (m, 2H, H-2), 1.51 (m, 1H, 3-OH)); $^{13}$C-NMR (CDCl$_3$, 125 MHz) δ=156.64, 153.54, 143.73, 135.16, 129.17, 126.20, 122.95, 111.72, 68.12, 58.41, 40.55, 31.87; FABMS (NBA), m/e 363 [(M+H)$^+$]; HRMS calcd for C$_{17}$H$_{21}$O$_4$N$_3$PS [(M+H)$^+$] 363.1262, found 363.1253.

Compound 2c (butylene linker). Compound 2c was prepared from 1,4-butanediol (420 μL, 4.74 mmol) by the procedure for 2a. The crude product was purified by column chromatography (SiO$_2$, CH$_2$Cl$_2$:AcOEt=5:1) to give 2b (169 mg, 76% as a red powder). $^1$H-NMR (CDCl$_3$, 200 MHz) δ=7.89 (m 6H, ArH (dabsyl)), 6.70 (m, 2H, ArH (dabsyl)), 4.06 (t, 2H, H-1, J=6.0 Hz), 3.56 (t, 2H, H-4, J=5.6 Hz), 3.07 (s, 6H, CH$_3$ (dabsyl), 1.72 (m, 4H, H-2, H-3), 1.24 (m, 1H, 4-OH); $^{13}$C-NMR (CDCl$_3$, 125 MHz) 156.31, 153.82 143.55, 135.23, 129.14, 126.24, 122.90, 111.74, 71.14, 61.93, 40.54, 28.65, 25.70, 25.89; FABMS (NBA), m/e 378 [(M+H)$^+$]; HRMS calcd for C$_{18}$H$_{24}$O$_4$N$_3$S [(M+H)$^+$] 378.1482, found 378.1473.

Compound 3a (ethylene linker). A solution of 2a (130 mg, 372 μmol), N,N-diisopropyl methyl phosphoramidic chloride (91 μL, 445 μmol) and diispropylehtylamine (97 μL, 557 μmol) in CH$_2$Cl$_2$ (5 mL) was stirred for 1 hour and evaporated. The crude product was purified by column chromatography (SiO$_2$, hexane:AcOEt:Et$_3$N=2:1:0.005) to give 3a (78 mg, 41% as a red oil). $^1$H-NMR (CDCl$_3$, 200 MHz) δ=7.96-7.81 (m 6H, ArH (dabsyl)), 6.68 (m, 2H, ArH (dabsyl)), 4.14 (t, 2H, H-1, J=5.4 Hz), 3.76 (m, 2H, H-2), 3.34 (m, 2H, CH (isopropyl)), 3.29 (m, 3H, OCH$_3$), 3.05 (s, 6H, CH$_3$ (dabsyl)), 1.08 (m, 12H, CH$_3$ (isopropyl))); $^{13}$C-NMR (CDCl$_3$, 125 MHz) δ=156.61, 153.48, 143.79, 135.33, 129.24, 126.14, 122.88, 111.69, 70.35, 70.28, 61.15, 61.00, 50.97, 50.83, 43.11, 43.02, 40.55, 24.93, 24.89, 24.87; FABMS (NBA), m/e 510 [(M+H)$^+$]; HRMS calcd for C$_{23}$H$_{35}$O$_5$N$_4$PS [(M+H)$^+$] 510.2058, found 525.2066.

Compound 3b (propylene linker). Compound 3b was prepared from 2b (200 mg, 550 μmol) by the procedure for 3a (196 mg, 68% as a red oil). $^1$H-NMR (CDCl$_3$, 500 MHz) δ=7.96-7.81 (m 6H, ArH (dabsyl)), 6.78 (m, 2H, ArH (dabsyl)), 4.23 (dt, 2H, H-1, J=1.5, 6.5 Hz), 3.67 (m, 2H, H-3), 3.51 (m, 2H, H-2), 3.36 (m, 3H, OCH$_3$), 3.14 (s, 6H, CH$_3$ (dabysl)), 1.98 (m, 2H, CH (isopropyl)), 1.15 (m, 12H, CH$_3$ (isopropyl))); $^{13}$C-NMR (CDCl$_3$, 125 MHz) δ=156.56, 153.47, 143.77, 135.36, 129.16, 126.12, 122.91, 111.68, 68.13, 59.22, 59.07, 50.78, 50.64, 42.98, 42.89, 40.54, 31.06, 31.00, 24.95, 24.90; FABMS (NBA), m/e 525 [(M+H)+]; HRMS calcd for C$_{24}$H$_{38}$O$_5$N$_4$PS [(M+H)$^+$] 525.2306, found 525.2301

Compound 3c (butylene linker). Compound 3c was prepared from 2c (1.12 g, 2.96 mmol) by the procedure for 3a (1.2 g, 75% as a red oil). $^1$H-NMR (CDCl$_3$, 200 MHz) δ=7.86 (m 6H, ArH (dabsyl)), 6.70 (m, 2H, ArH (dabsyl)), 4.05 (t, 2H, H-1, J=6.0 Hz), 3.60-3.42 (m, 4H, H-4, CH (isopropyl)), 3.31 (m, 3H, OCH$_3$), 3.07 (s, 6H, CH$_3$ (dabsyl)), 1.66 (m, 4H, H-2, H-3), 108 (m, 12H, CH$_3$ (isopropyl))); $^{13}$C-NMR (CDCl$_3$, 125 MHz) δ=156.56, 153.469, 143.79, 135.46, 129.15, 126.31, 122.90, 111.69, 70.95, 62.68, 62.54, 42.96, 42.86, 40.55, 27.46, 27.405, 29.93, 24.98, 24.92, 24.90, 24.09, 22.96; FABMS (NBA), m/e 539 [(M+H)$^+$]; HRMS calcd for C$_{25}$H$_{39}$O$_5$N$_4$PS [(M+H)$^+$] 539.2470, found 539.2457.

Synthesis of unmodified oligonucleotides. All oligonucleotides were synthesized on 1 μmole scale on an ABI model 392 synthesizer using standard β-cyanoethylphosphoroamidite coupling chemistry. Deprotection and cleavage from CPG support was carried out by incubation in concentrated ammonia for 14 h at 55° C. Following deprotection, oligonucleotides were purified by PAGE, and quantitated by UV absorbance using the nearest neighbor approximation to calculate molar absorptivities.

Preparation of dabsyl- and fluorescein-labeled oligonucleotides. Pac-protected dA, iPr-Pac-preotected dG, and acetyl-protected dC phosphoroamidites for ULTRA MILD SYNTHESIS (Glen Research) were employed in synthesizing oligonucleotides containing a dabsyl group. The fluorescein label was introduced with fluorescein-dT phosphoroamidite (Glen Research). Deprotection and cleavage from the CPG support was carried out by incubation in 0.05 M potassium carbonate in methanol for 6 h at room temperature. After concentration, oligonucleotides were purified by reverse-phase HPLC (Allotec BSD-C18 column 250 mm, eluting with 0.1 M triethylammonium acetate pH 7.0/acetonitrile). Probe structures were confirmed by MALDI-TOF mass spectrometry. (SEQ ID NO:1)$^{Dab-ethyl}$-GT$^{FAM}$GGGCAGAGT: calculated mass, C$_{165}$H$_{191}$N$_{57}$O$_{82}$P$_{12}$S 4688.4; found 4706.8. (SEQ ID NO:1)$^{Dab-propyl}$-GT$^{FAM}$GGGCAAGAGT: calculated mass C$_{166}$H$_{193}$N$_{57}$O$_{82}$P$_{12}$S 4702.4; found 4720.0. (SEQ ID NO:1)$^{Dab-butyl}$-GT$^{FAM}$GGGCAAGAGT: calculated mass 4716.4; found 4733.5. For 3'-Phosphorothioate sequences, the first nucleotide added after the phosphorylation reagent was sulfurized by the sulfurizing reagent (Glen Research). 5'-$^{32}$P labeling was carried out using T4 polynucleotide kinase (NEB) and γ-$^{32}$P-ATP (Amersham).

Dabsyl-mediated autoligation on beads. 3'-phosphorothioate oligonucleotide immobilized on PEG-polystyrene beads was incubated in 50 μL pH 7.0 PIPES (70 mM) buffer containing 10 mM MgCl$_2$ and 50 μM dithiothreitol with 50mer target DNA (1 nM) and Dabsyl-labeled 8mer probes (10 μM) at 30° C. for 24 h. After incubation, 20 μL of reaction suspension containing the beads was spotted on a glass slide. Fluorescence images were obtained through an epifluorescence microscope (Nikon Eclipse E800) with high-pressure mercury lamp (Nikon model HB-10103AF), using a SPOT RT digital camera and SPOT imaging software. Microscopes setting are as follows. Fluorescein: ex. 460-500. Digital camera settings are as follows. Image: black&white mode, 8 bpp (monochrome), clear filter; exposure time=100 msec, binning=no, gain=2. Images were false colored green, using SPOT imaging software.

Oligonucleotide probes. Oligodeoxynucleotides were synthesized with β-cyanoethylphosphoroamidite chemistry, and purified by PAGE gels. Dabsyl and fluorescein-modified oligonucleotides were prepared following literature procedures, and characterized by mass spectrometry.

Dabsyl-mediated autoligation reactions. Ligations were performed in 3 mL pH 7.0 PIPES (70 mM) buffer containing 10 mM MgCl$_2$, 50 μM dithiothreitol with target nucleic acid (100 nM), 7mer 3'-phosphorothioate probe (100 nM) and Dabsyl-labeled 8mer probes (100 nM respectively) at 25° C.

for 2 h. Reactions were observed by fluorescence spectrometer (Fluorolog 3-11, Jobin Yvon-SPEX). In order to observe kinetics of ligation reactions, fluorescence intensity was measured with 5 sec integration at 1 min intervals: excitation was at 494 nm, and the fluorescence of FAM was measured at 518 nm. Reactions using radiolabeled probes were incubated at the indicated temperatures and times. Samples were heated to 95° C. for 2 min and loaded on 20% polyacrylamide gel containing 8 M urea. Radioactivity on gels was quantitated on a Molecular Dynamics Phosphorimager (Amersham).

Reactions on PEG-polystyrene beads were carried out using 3'-phosphorothioate oligonucleotide immobilized on PEG-polystyrene beads. They were incubated in 50 μL pH 7.0 PIPES (70 mM) buffer containing 10 mM $MgCl_2$ and 50 μM dithiothreitol with 50mer target DNA (1 nM) and dabsyl-labeled 8mer probes (10 μM) at 30° C. for 24 h.

Results and Discussion

The principle of product destabilization in probe design. The molecular approach used here for detection of genetic sequences relies on the principle of the self-directed reaction of a probe and a tether bound to a target strand of DNA or RNA (FIG. 1). The reaction of the nucleophilic phosphorothioate group on one probe with the 5' electrophilic carbon of the adjacent probe causes displacement of a dabsylate group, which acts both as a fluorescence quencher and a leaving group. This results in formation of a bond between the two probes, yielding a double-stranded segment as long as the combination of the two starting probes. Since a fluorescent label is also present on the electrophilic DNA probe, the loss of the dabsylate quencher results in an increase in fluorescence as probes become ligated. Because the probes are short, their binding to mismatched targets is weak, allowing the method to give high selectivity for single nucleotide differences.

Previous designs placed a dabsylate group directly on the 5' hydroxyl of the electrophile oligonucleotide probe (FIG. 1B) (Sando and Kool (2002) supra.) The ligation reaction then resulted in a linkage between the two probes that was very nearly the same as that in natural DNA, the only difference being that one bridging oxygen was replaced by sulfur. This small difference causes little or no destabilization to the DNA helix (Xu and Kool (1999), supra.) Thus the ligation results in two weakly-binding probes being converted to a longer tightly-binding oligonucleotide, which is strongly inhibited from dissociating from the target DNA. For example, if one compares binding of complementary DNA by two previously studied 7mer+13mer half-probes to that of the expected 20mer ligated product, the $T_m$ is calculated to rise from ca. 60° to 85° C., and binding affinity is expected to become much more favorable, by at least several kcal/mol. In practical terms, this limits the signal formed per target molecule to not much greater than one under isothermal conditions. Although technically the target might act as a catalyst for ligation of probes, the catalysis suffers from strong product inhibition.

The new molecular design presented here offers a strategy for overcoming this product inhibition, by selectively destabilizing the ligated product compared to the previous sulfur-bridged linkage (FIG. 1A). In this new approach, the electrophilic dabsylate group is placed at the end of a hydrocarbon linker chain, which is in turn linked to the 5' end of the electrophile probe via phosphoramidite chemistry (FIG. 1A; universal linkers). This 5' linker is not expected to cause strong changes in binding by this oligonucleotide prior to reaction. Models suggest also that a nucleophile probe should be able to bind adjacent (coaxial) to the electrophile probe with little difficulty. As a result, one might expect this linker to make little difference to the energy of the starting probe/target complex. After ligation, the situation is different, however: the ligated probe now contains a several-atom-length flexible linker interrupting the two complementary half-segments that are complementary to adjacent positions on the target. This complex is expected to be considerably less favorable entropically than having a direct linkage between the two half-probes. For example, abasic linkers are known to destabilize DNA markedly. Thus, the ligated probe/target complex is expected to dissociate much more readily than in the previous directly-linked approach, even under isothermal conditions. This dissociation can allow, if desired, a new pair of probes to bind, generating multiple signals per target.

Linker probe design. To test this, we constructed a series of three linkers of varying length, based on ethylene glycol (DEt), 1,3-propanediol (DPr) and 1,4-butanediol (DBu) (see FIG. 1A). These are expected to change the energy of the ligated product complex, and also possibly change the rate at which ligation occurs, by offering varied distances and geometries relative to the phosphorothioate nucleophile. Dabsylate was placed at one end of each diol linker, and an O-methyl phosphoramidite at the other. The O-methyl group was chosen because early studies with the standard cyanoethyl group suggested that the phosphate anion (generated after deprotection) could react intramolecularly with the arylsulfonate function, generating background signals even in the absence of target. The O-methyl group was found to strongly diminish this background reactivity. To preserve the potentially labile methyl triester we used mild deprotection conditions and employed Pac-protected phosphoramidites in the probe synthesis (Myers et al. (1995) J. Biol. Chem. 270, 6664-6670; Iver et al. (1995). J. Org. Chem. 60, 8132-8133).

For comparison we also tested probes designed to generate bulges with the target. Bulged nucleotides also are known to destabilize segments of perfectly complementary double helices, and so we designed different bulge geometries to test: a case with an extra nucleotide in the probe strand, and one with an extra nucleotide in the target (FIG. 1B). Finally, we also tested for comparison a pair of perfectly complementary probes with the previously described 5'-dabsylate group situated directly on the 5'-hydroxyl (abbreviated DT). That class of probe generated only ca. one signal per target at moderate target concentrations, although small amounts of turnover were previously observed with a similar iodide-activated case at low target concentrations.

Ligation rates. Ligation reactions were carried out in PIPES buffer (pH=7) containing 10 mM $MgCl_2$. Relative rates of reaction were compared at equimolar target and probe concentrations (100 nM each), and the progress was followed in solution by the increase in fluorescence signal. The results are shown in FIG. 2. The data showed that, under these conditions, all three new linkers (DEt, DPr and DBu) gave ligation that was more rapid than that for the previous dabsyl-thymidine case (DT) in FIG. 2A. The most rapid was the DBu case (FIG. 1), which ligated at a rate ca. four-fold higher than the previous directly linked 5'-dabsyl approach (DT), based on initial slopes of the curves. The DPr case was ca. three-fold faster, while the DEt case was faster than the DT by a small factor of ~1.2. A possible explanation for this is that the geometry in the DT case is suboptimum for the displacement reaction, and that the flexibility of the new linkers increases the likelihood of reaching a favorable geometry.

We also evaluated the ligation rates for the bulge-geometry strategies with the previous standard, the DT probe (FIG. 2B). Here the data clearly showed that either a bulge in the probes (DT+thio3) or a bulge in the template (DT+thio2) slowed the rate considerably, by a factor of 3.2. Both bulge geometries yielded similar rates. One might expect the extra nucleotide either to block the ability to reach a favorable geometry for reaction, or to add unfavorable free energy at the transition state by disrupting base local base pairing or stacking.

In a third experiment, we examined the effect of combining different nucleophile probes with the DPr linker case. This was done because with the new linkers it is not clear whether a linker should be considered as a proxy for a nucleotide or not (note that the three carbon chain is the same number of carbons as a deoxyribose residue in a DNA backbone). When we compared the relative rates for the three cases (FIG. 2C), we observed that the case where the linker is considered extraneous to the pairing (DPr+thio3) was by far the fastest at ligation. It showed a better than 7-fold advantage in rate compared to the other two alignments (DPr+thiol, DPr+thio2).

Finally, we compared the rates for ligation with the new linkers when the target is complementary or mismatched by a single nucleotide. In this experiment, the mismatch (C/A) was situated at the center of the heptameric nucleophile probe binding site. The results showed (FIG. 2D) that the rate was indeed sensitive to a single mismatch, with a 12.3-fold drop in ligation rate with the DBu linker on the mismatched target, and a 9-fold drop with the DPr linker. This order-of-magnitude selectivity is comparable to sequence selectivities observed for other methods, although it is smaller than was reported previously for 5'-iodide-mediated autoligating probes. The origin of this difference is unclear, but may arise from differences of analytical methods between gel electrophoresis (in which background is substracted) and fluorescence spectrometer (which includes background).

Figure 8:
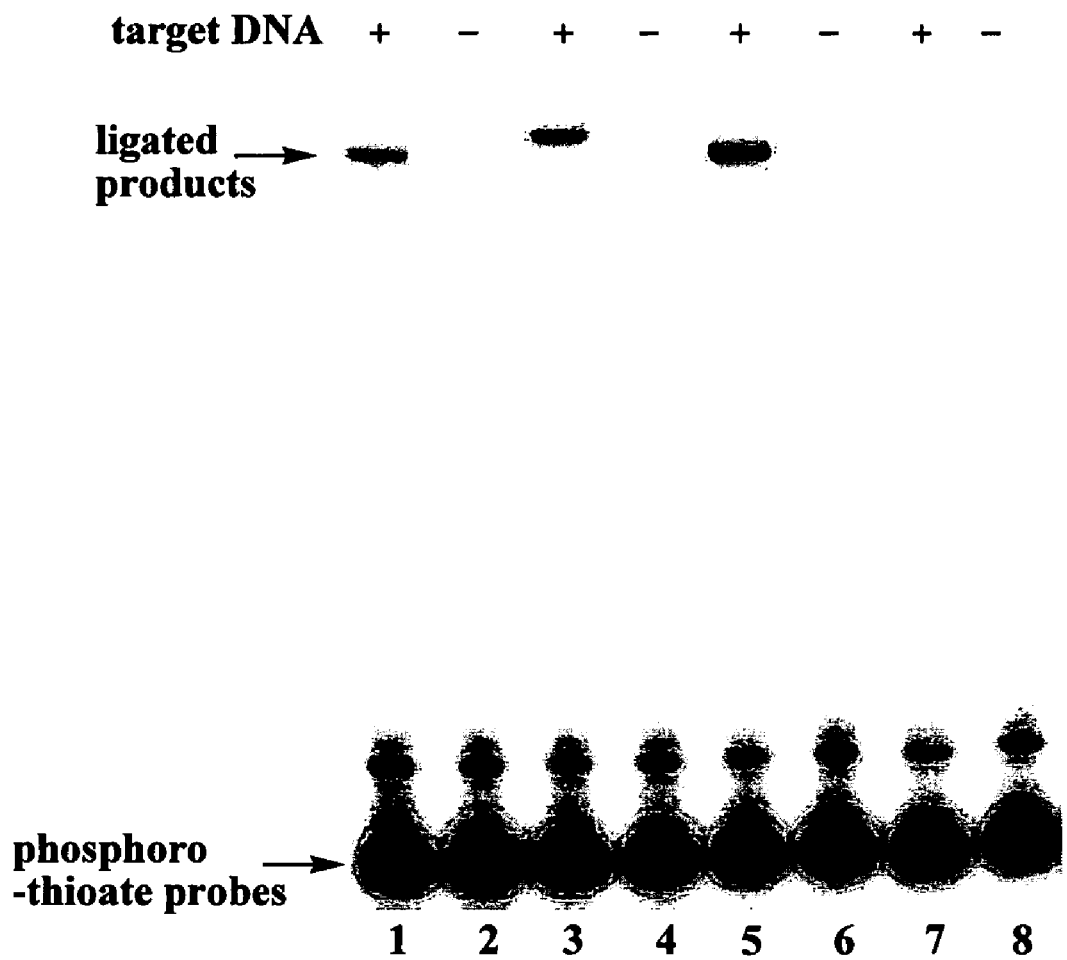
FIG. 8. Analysis of dabsyl-mediated autoligations by 20% polyacrylamide gel electrophoresis. The radioactivity in the ligated product bands was quantitated by digital phosphorimaging. Ligation reactions were carried out in a pH 7.0 buffer (70 mM tris-borate) containing 10 μM dabsyl probe, 10 μM phosphorothioate probe (thio4) and 10 mM $MgCl_2$ with or without 10 nM target DNA at 25° C. for 24 h. Lane1, 2: Bu40, lane3, 4: Bu41, lane 5,6:Bu42, lane 7,8: DT40.

Measurement of turnover. Turnover, and the associated signal amplification, is useful when target concentrations are low. Under these conditions, one would typically use a large excess of probes relative to numbers of targets. To measure turnover with the current probes we compared the number of equivalents of signal with moles of target. This required the development of a method for carefully quantitating the signal, and confirming that the signal arises from true template-dependent intermolecular ligation reactions rather than from background sources such as (i) incomplete quenching of fluorescence by dabsyl; (ii) hydrolysis or other release of dabsylate from the electrophile probe; or (iii) intermolecular ligation independent of the template strand. To evaluate this we performed ligations using radiolabeled phosphorothioate probes at varied target concentrations and temperatures (see below), and we separated products from excess unreacted probes by gel electrophoresis. An image of such a gel is shown FIG. 8. The radioactivity in the ligated product bands was quantitated by digital phosphorimaging. We first prepared a standard dilution curve to make a calibration plot of radioacitivity as a function of the amount of $^{32}$P-labeled phosphorothioate oligonucleotide in a gel lane. This plot showed good linearity, and allowed us to take a given signal and, from the plot, extract the number of moles of radioactive oligonucleotide product in a given band on the gel.

Effect of target concentration on amplification. The turnover of ligated products from the target RNA or DNA is expected to increase as the concentration of target decreases. To test this, we varied target concentrations over the range 1000 nM-1 nM. The butanediol-type universal linker probes were used for turnover measurement since this linker yielded the most rapid ligations. The probe concentrations were held constant at a considerable excess (10 μM), and the reactions were evaluated at 25° C. after relatively long incubations of 24 h. To ensure that signal was not the result of template-independent ligations or hydrolysis, we subtracted background signals from identical reactions lacking templates (see FIG. 8).

The target concentration effect was measured for universal butanediol (DBu) linkers as well as for the original dabsyl-T electrophile (FIG. 3). The position of the 8mer butanediol linker probe on the template was shifted relative to the 7mer phosphorothioate probe, yielding ligated products with different bulged complementarity (Bu40, Bu41, Bu42). The results showed (FIG. 4) that for all four cases significant amounts of turnover was observed, and for all four there was a marked increase in turnover with lowering target concentration. At the lowest concentration, the number of turnovers was least for the DT40, with maximum turnovers of ca. 8-fold at the 1 nM target concentration. However, the universal linker cases showed considerably higher turnover numbers. The coaxial case (Bu40, where the linker is extraneous to the sequence) was the lowest, but still yielded up to 25 equivalents of signal per target; the case in which probes skip a base (Bu42, yielding a bulge in the target strand) was most efficient of all, yielding 92 turnovers. The case in which the probes are overlapped (Bu41, yielding a 1-nt bulge in the probes) fell between the two, at 39 turnovers. Thus we conclude that, of all the new molecular strategies, the Bu42 case yields the most efficient turnover under these conditions.

These data demonstrate the benefits of the compositions of the invention, which react in a variety of configurations, including non-contiguous binding to a target.

Effect of temperature. The temperature is expected to have significant effects both on ligation rates and turnover efficiency. Ligation chemistry may be expected to increase in rate with temperature; however, template binding by the unligated probes is expected to begin to melt at higher temperatures, which would remove the template effect and slow the rate again. As a result, one expects an intermediate temperature range, perhaps near the $T_m$ of the shorter probe, where a maximum in rate is reached.

Figure 9:
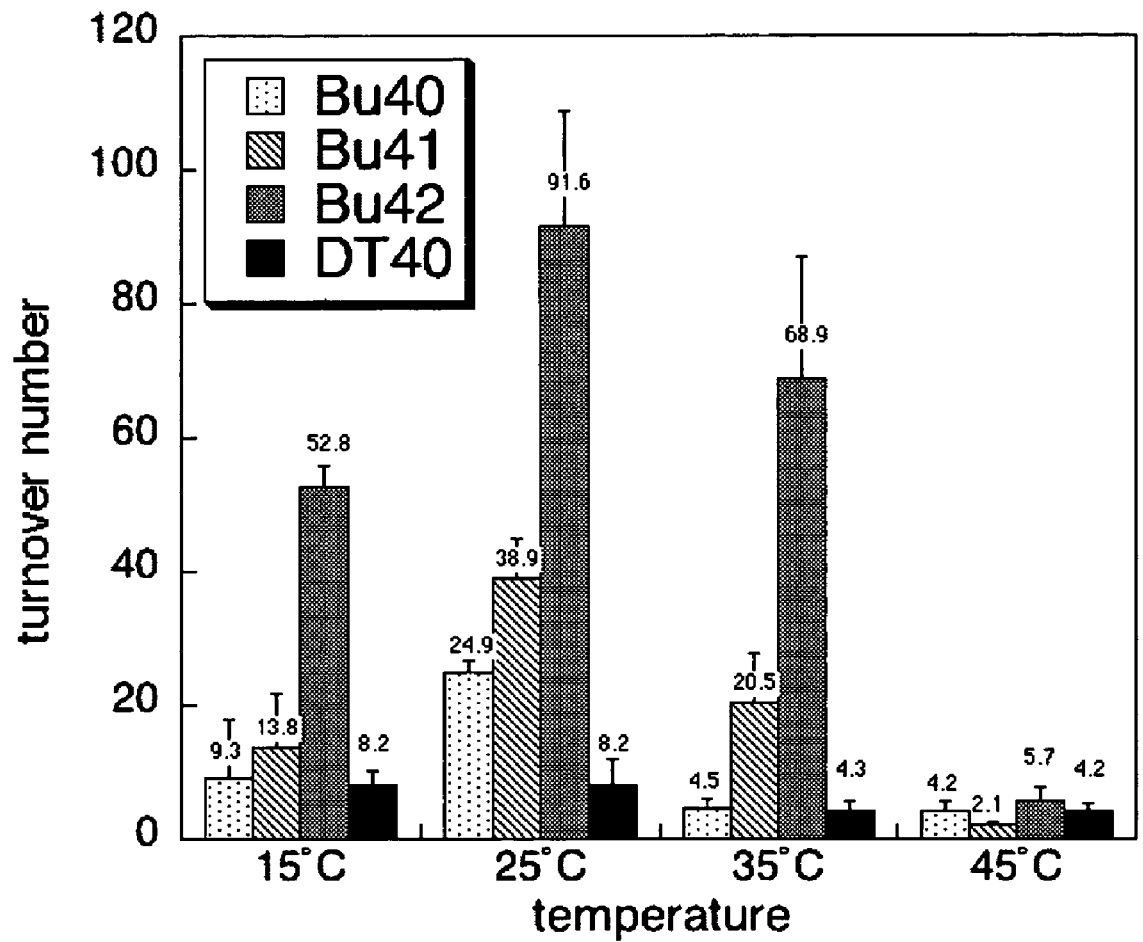
FIG. 9. Effects of reaction temperature on turnover. Reaction mixtures were incubated at 15°, 25° C., 35° C. or 45° C., and contained 10 μM dabsyl probe, 10 μM phosphorothioate probe, 1 nM target DNA and 10 mM $MgCl_2$ in a pH 7.0 buffer (70 mM Tris-borate buffer) for 24 h. The reactions were analyzed by 20% polyacrylamide gel.
Figure 10:
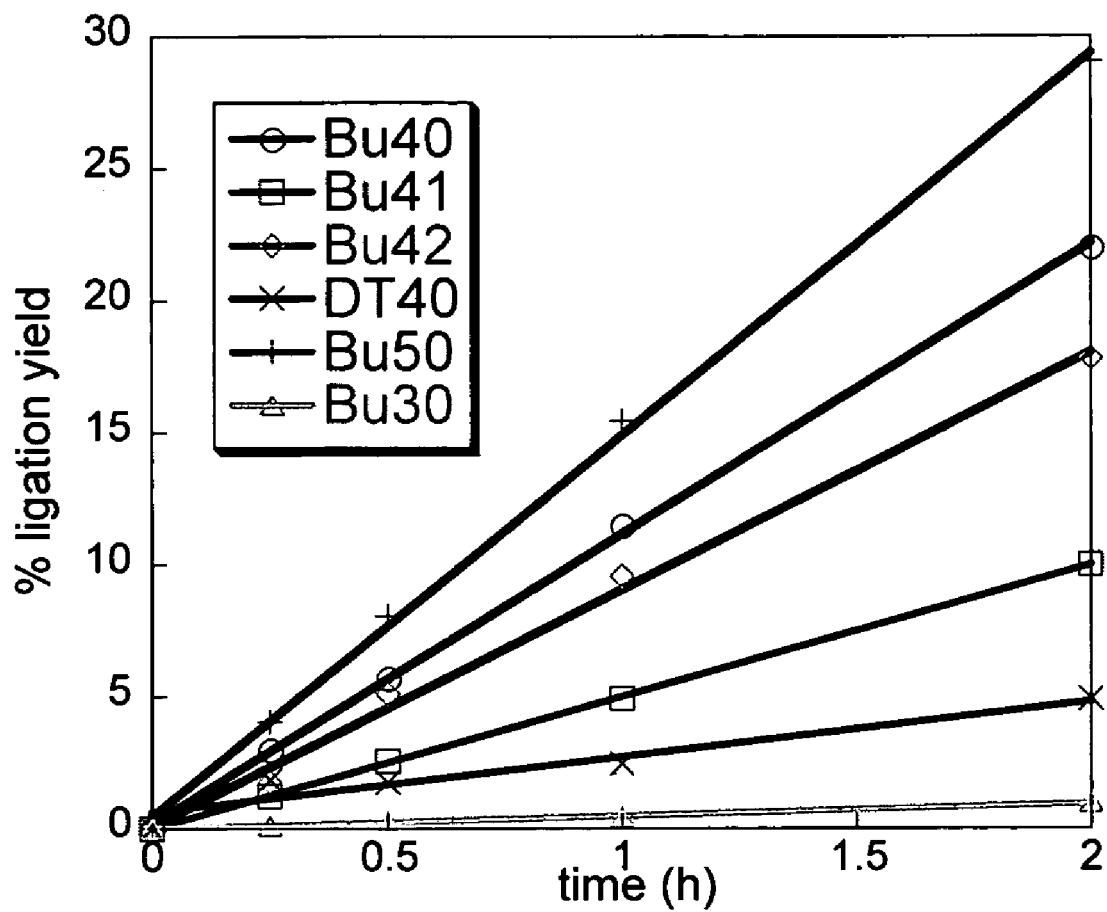
FIG. 10. Initial rates of ligation analyzed by 20% polyacrylamide gels: 1 μM of dabsyl probe, phosphorothioate probe and DNA target respectively, in pH 7.0 PIPES buffer (70 mM) containing 10 mM $MgCl_2$ at 25° C.

To test for such effects and optimize turnover, we carried out ligations in which we varied temperature over the range 15° to 45° C. in 10° increments (FIG. 9). As before, all four ligation chemistries were compared. For most cases we observed an increase in turnover efficiency with increasing temperature, going through a maximum, then dropping at the highest temperatures. The original DT40 probes gave very little turnover at any temperature. Once again, the case in which the probes yield a bulge in the target strand (Bu42) proved to be most effective, giving as high as 92 turnovers at optimum temperature, 25° C. For most cases, maximum turnover was seen at 25° C. and least turnover at 45° C.

Effect of probe length. The probe length is also expected to have significant effects both on ligation rates and turnover efficiency. Lengthening probes should result in more significant product inhibition, as dissociation would be greatly slowed. On the other hand, longer probes should rapidly ligate based on strong hybridization. To test this, we designed a short probe pair and a long probe pair, which yield ligation product with bulge structure (Bu30/thio-5 and Bu50/thio-6, respectively) (FIG. 3). The ligation rate with the 12-mer probe Bu50 was 30-fold greater than the 6-mer probe Bu30, and 1.3 fold greater than the 7-mer (SI, FIG. S3). However, the longest and shortest probes gave lower turnover number (6-7) than the 7mer in 24 h. Thus, we conclude that probes that are too short or too long are unfavorable for turnover, due to slow ligation or strong product inhibition respectively.

Testing ligation on an RNA target. Because RNA-DNA duplexes form different helical structure than DNA-DNA duplexes, there is no guarantee that such ligation chemistry would proceed the same in detecting RNA as compared to DNA. Indeed, the prior art has failed to demonstrate ligation on an RNA target.

Figure 5:
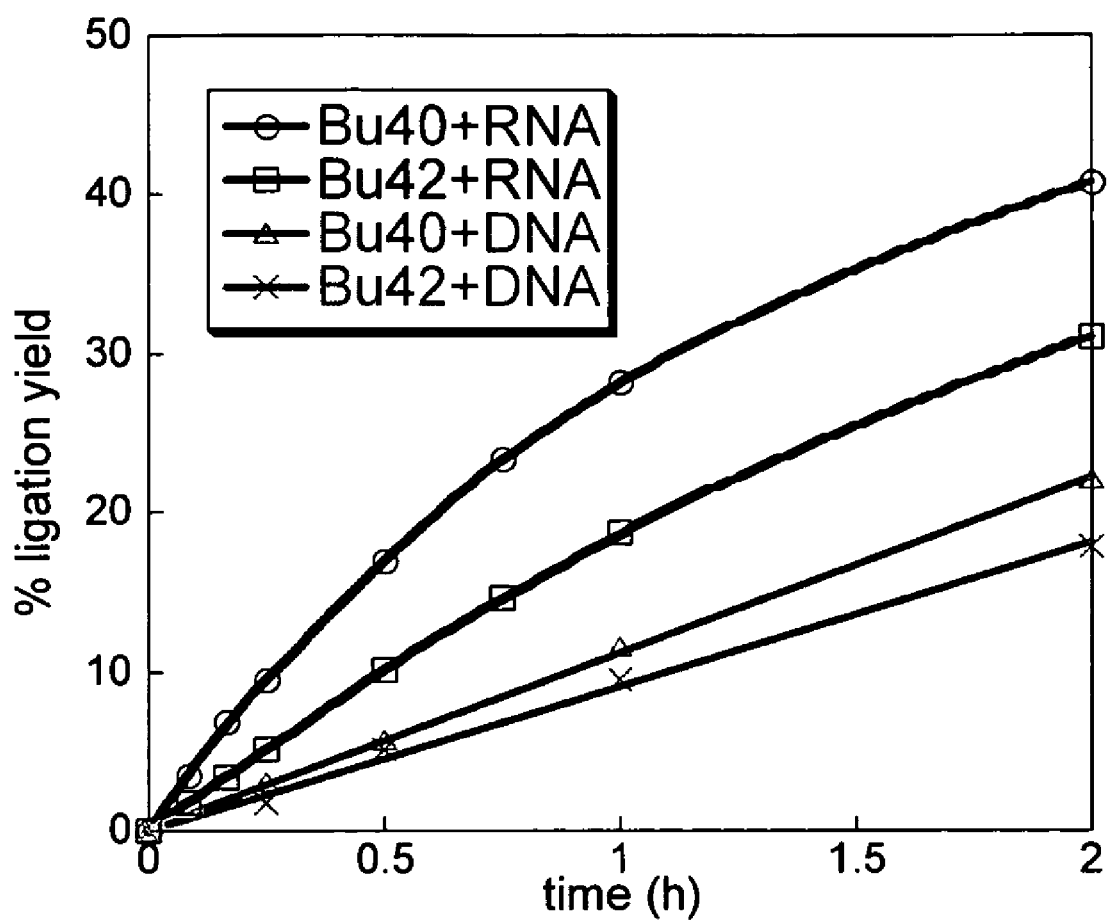
FIG. 5. Comparison of ligation rates with RNA vs. DNA templates. Ligations were carried out under the following conditions: Linker probe: 1 μM, thio4: 1 μM, RNA or DNA template: 1 μM at 25° C.
Figure 6:
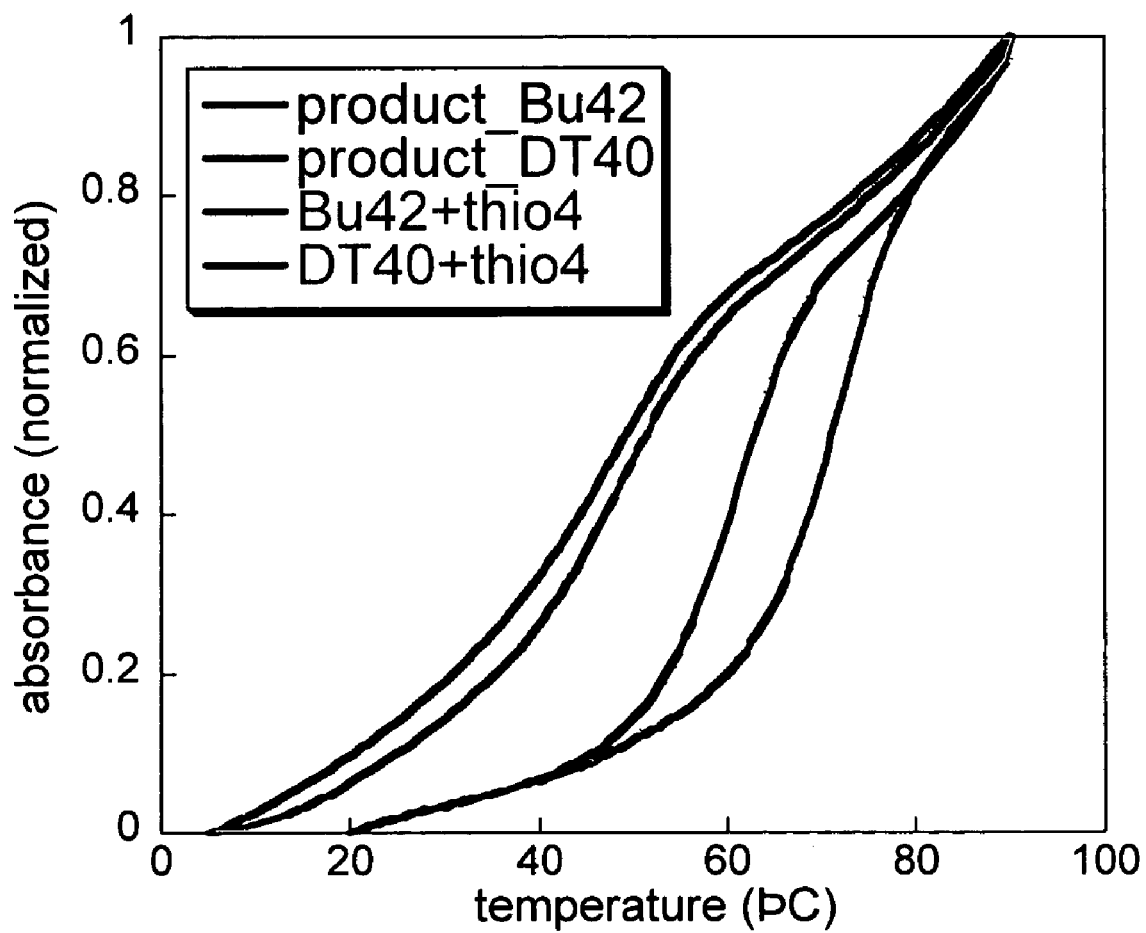
FIG. 6. Thermal stability of unligated probes and ligated products, showing destabilization by universal linker. Ligated product from Bu42 and DT40 were isolated and tested for binding of target DNA. Conditions: 2.5 μM oligonucleotide, 10 mM $MgCl_2$ in pH 7.0 PIPES buffer (70 mM). Absorbance changes were normalized.

Thus we prepared an RNA target and compared reaction rates with the previous DNA target. Interestingly, ligation rates on the RNA template were more rapid than the corresponding DNA template (FIG. 5). Using initial rates, the Bu40 and Bu42 cases were faster than with the DNA target by factors of 2.9 and 3.2, respectively. The turnover number of Bu42 on the RNA template was 78 at 25° for 24 h, similar in magnitude to the number on the DNA template.

The data demonstrate that the present compositions provide an effective method of detecting the presence of a target sequence in an mRNA sample. It is known in the art that enzymes capable of catalyzing DNA ligation work poorly on RNA; and chemical ligation strategies from other laboratories have not been shown to be effective with an RNA template.

Analysis of destabilization by the alkanediol linkers. Our initial hypothesis was that turnover in this self-ligation reaction would be favored when the ligated product does not bind well to the template. To evaluate this we isolated ligated 15mer products, for the original dabsyl-T linkage from DT40 (shown here to turn over poorly) and the butanediol-linked case Bu42 (the most effective turnover case). We measured binding of these products to a target DNA by thermal denaturation. The results showed that the melting temperature of combined unligated probe pairs for the two cases was essentially the same (45° C.); however, the ligated product from Bu42 (Tm=58.5° C.) was much more destabilized with target DNA than was the product from DT50 (Tm=70.7° C.). This adds support to our product destabilization hypothesis, and suggests that efforts aimed at even greater product destabilizations may be warranted in the future.

Self-ligation and turnover on solid support. Bead-supported and glass-supported genetic detection methods are now widespread. We have previously demonstrated that under non-turnover conditions, a bead-supported nucleophile probe could ligate dabsyl-quenched probes to themselves in the presence of template DNA. This was done with dabsyl-T electrophiles, which the present results show to be poor at turnover. It would be of considerable utility in some applications if turnover were also possible on the beads or arrays: one template could be passed from probe to probe on the bead surface, again generating multiple signals per equivalent of template and amplifying signals that are otherwise weak.

Figure 7:
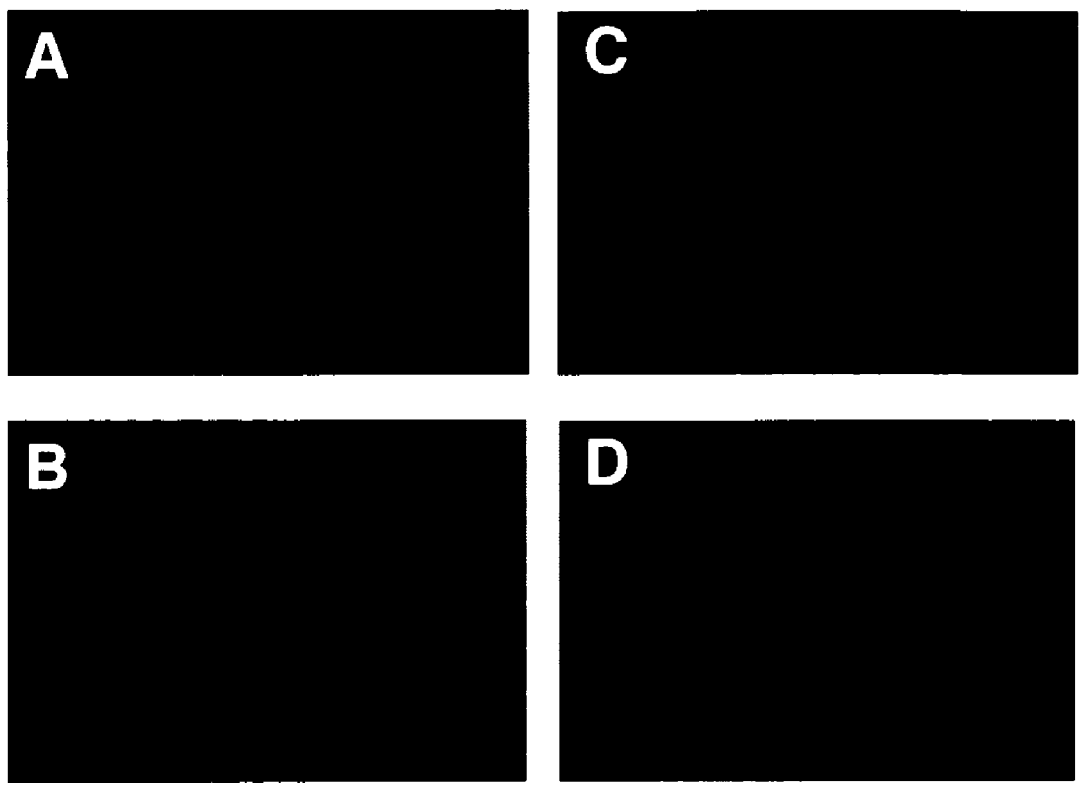
FIG. 7. Signal amplification during DNA detection on solid support. Ligation reactions were done on phosphorothioate-conjugated (CGGTGCGs) beads using 10 μM butanediol linker probe Bu42 (A) with 1 nM target or (B) without target DNA, or 10 μM DT40 probe (C) with 1 nM target or (D) without target DNA at 30° C. for 24 h. No washing to remove unreacted probes was done after ligations.

To test this possibility we prepared PEG-polystyrene beads with a phosphorothioate-derivatized oligonucleotide probe with its 3' terminus free (by application of reverse 5'->3' oligonucleotide synthesis). We reacted these beads in the presence of target DNA, with either the original dabsyl-T probe or the butanediol-universal-linked dabsyl probe, which was shown (above) to be most proficient at turnover. FIG. 7 shows beads after 24 hours incubation with Bu42 (A) and DT40 (C). The beads treated with Bu42 were brighter than those with DT40 by a factor of 17. Little signal was seen from beads without target DNA (FIGS. 7B, D). In addition, background fluorescence remained low; thus no washing of the beads was required, making the method exceedingly simple. Thus, we conclude that the ability to undergo multiple turnovers results in a marked difference of signal intensity on beads with the new universal linker.

Implications in probe design and application. The new linkers, particularly the butanediol and propanediol-based quenched linkers, offer significant advantages over previous self-ligating probe chemistries. These two optimum cases offer more rapid rates than previous quencher-activated probes. For example, under equimolar probe-target conditions, the butanediol case reaches 30% yield within 120 min, compared to 12 hr with the dabsyl-T activation. Under excess probe (turnover) conditions, the butanediol linker offers tenfold signal amplification in as little as 160 min, and >90-fold in 24 h. Importantly, RNA detection was even more rapid than DNA detection, a result that is markedly different from enzymatic ligations, where RNA is a poor target.

Unlike previously described methods, the linkers of the present invention are quite simple and inexpensive to prepare, and they can be appended to any DNA oligonucleotide in automated steps on a standard DNA synthesizer. In addition, the hydrophobicity of the dabsyl group offers ease of purification by reverse-phase HPLC, in analogy to the widely used "trityl on" purification strategy. A previous limitation of the earlier dabsyl-mediated ligations was the requirement for a 5'-thymine on the electrophile probe, which resulted in some sequence limitations. The new approach can be applied universally to any probe sequence, and thus any target site. This ease of preparation and application increases the utility of the self-ligating probe strategy.

In addition to the ease of synthesis and enhanced reaction rate, the turnover observed for the new probes offers significant utility in detection/identification of target RNAs and DNAs when copy number or concentration is low. For example, the universal quenched linker strategy may be used for qualitative identification and imaging of RNAs in cells. In contrast to previously described approaches, the methods of the present invention are isothermal, and yield amplification of nearly two orders of magnitude. The present methods readily generate easily detectable fluorescence signals, and can be used in a multicolor format.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved.

What is claimed is:

1. A modified polynucleotide having the structure:

$$Z-L-T-O-\overset{\overset{O}{\|}}{\underset{R}{P}}-A \qquad III$$

wherein T is a tether selected from the group consisting of:

where n is from 2 to 20; and $n_1$ and $n_2$ are independently selected to be from 1 to 20; wherein $n_1+n_2$ are usually not more than about 20; and y is from 1 to 7;

and wherein T is optionally substituted with an alkyl, aryl, alkenyl, aralkyl, aralkenyl, cycloalkyl, cycloalkylalkyl or cycloalkylalkenyl group;

$R^3$ is selected from an alkyl, usually branched or linear lower alkyl; hydroxy, alkoxy, aryloxy, haloalkoxy, cyano, nitro, mercapto, alkylthio, —S(O)$_p$R$^6$ (where p is 0 to 2), —S(O)$_p$N(R$^6$)$_2$ (where p is 0 to 2); —OR$^6$, —C(O)OR$^6$, —C(O)N(R$^6$)$_2$, —N(R$^6$)$_2$, —N(R$^6$)C(O)OR$^7$, —N(R$^8$)C(O)R$^8$, and —R$^8$—N=N—O—R$^7$;

where each $R^6$, $R^7$ or $R^8$ is independently selected from the group consisting of hydrogen, alkyl, alkenyl, haloalkyl, haloalkenyl, aryl, aralkyl, aralkenyl, cycloalkyl, cycloalkylalkyl and cycloalkylalkenyl;

L is an activated leaving group selected from sulfonyl, carbonyl esters, para nitrophenyl esters, nitrophenyl esters, trifluoroacetyl esters, nosylate, brosylate, tosylate, perchlorate, triflate, and mesylate;

Z is a fluorophore or quencher;

A is a nucleotide of at least 6 bases in length and not more than about 100 bases in length; and R is OR$^1$ or O$^-$; wherein R$^1$ is a linear or branched lower alkyl.

2. The modified polynucleotide of claim 1, wherein L is a group selected from sulfonyl, carbonyl esters, para nitrophenyl esters, nitrophenyl esters, trifluoroacetyl esters, nosylate, brosylate, tosylate, perchlorate, triflate, and mesylate.

3. The modified polynucleotide of claim 1 wherein Z is a quencher, and said polynucleotide further comprises at least one fluorophore quenched by Z.

4. A composition comprising a pair of polynucleotides, wherein said first polynucleotide is a modified polynucleotide according to claim 1, and said second polynucleotide comprises a 3' nucleophilic group.

5. A composition according to claim 4, wherein said first and said second polynucleotides hybridize to neighboring sites on a target sequence.

6. The composition of claim 4, wherein the nucleophilic group is a phosphorothioate or a phosphoroselenoate.

7. The composition of claim 4, wherein said second polynucleotide comprises at least one fluorophore.

8. A kit for the detection of a nucleic acid sequence of interest, the kit comprising a modified polynucleotide according to claim 1, and instructions for use.

9. A modified polynucleotide having the structure:

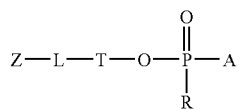

wherein:
Z is

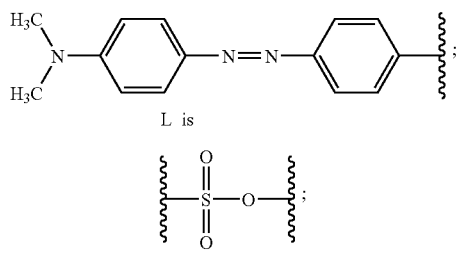

L is

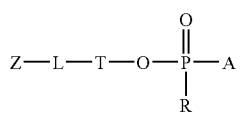

T is (CH$_2$)$_n$ where n is from 2 to 20;
R is OCH$_3$;
and A is any nucleotide or part of a polynucleotide.

10. A composition comprising a pair of polynucleotides, wherein said first polynucleotide is a modified polynucleotide having the structure:

$$Z-L-T-O-\overset{\overset{O}{\|}}{\underset{R}{P}}-A \qquad III$$

wherein T is a tether selected from the group consisting of:

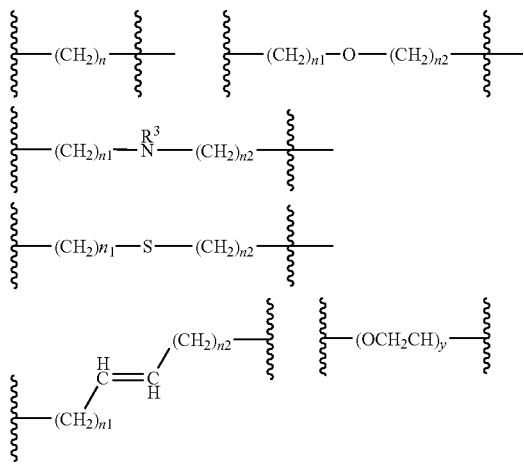

where n is from 2 to 20; and n$_1$ and n$_2$ are independently selected to be from 1 to 20; n$_1$+n$_2$ are usually not more than about 20; and y is from 1 to 7;
and wherein T is optionally substituted with an alkyl, aryl, alkenyl, aralkyl, aralkenyl, cycloalkyl, cycloalkylalkyl or cycloalkylalkenyl group;
R$^3$ is selected from an alkyl, usually branched or linear lower alkyl; hydroxy, alkoxy, aryloxy, haloalkoxy, cyano, nitro, mercapto, alkylthio, —S(O)$_p$R$^6$ (where p is 0 to 2), —S(O)$_p$N(R$^6$)$_2$ (where p is 0 to 2); —OR$^6$, —C(O)OR$^6$, —C(O)N(R$^6$)$_2$, —N(R$^6$)$_2$, —N(R$^6$)C(O)OR$^7$, —N(R$^8$)C(O)R$^8$, and —R$^8$—N=N—O—R$^7$; where each R$^6$, R$^7$ or R$^8$ is independently selected from the group consisting of hydrogen, alkyl, alkenyl, haloalkyl, haloalkenyl, awl, aralkyl, aralkenyl, cycloalkyl, cycloalkylalkyl and cycloalkylalkenyl;
L is an activated leaving group selected from sulfonyl, carbonyl esters, para nitrophenyl esters, nitrophenyl esters, trifluoroacetyl esters, nosylate, brosylate, tosylate, perchlorate, triflate, and mesylate;
Z is a fluorophore or quencher;
A is a nucleotide of at least 6 bases in length and not more than about 100 bases in length; and
R is OR$^1$ or O$^-$; wherein R$^1$ is a linear or branched lower alkyl;
and said second polynucleotide comprises at least one fluorophore or quencher, and comprises a 3' nucleophilic group;
wherein said first and said second polynucleotides hybridize to neighboring sites on a target sequence.

11. The composition of claim 4, wherein the nucleophilic group is a phosphorothioate or a phosphoroselenoate.

12. A modified polynucleotide according to claim 1, wherein Z is a fluorophore selected from fluorescein, 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), =2',7'-dimethoxy-4',5'-dichloro-6-carboxyfluorescein (JOE); Cy3, CY5, Cy5.5, a dansyl derivative; 6-carboxytetramethylrhodamine (TAMRA), a BODIPY fluorophore, tetrapropano-6-carboxyrhodamine (ROX), ALEXA dye, and Oregon Green.

13. A modified polynucleotide according to claim 1, wherein Z is a quencher selected from DABSYL (dimethylamino-azobenzene-sulfonyl) group, DANSYL (5-dimethylaminonaphthalenesulfonyl); DIMAPDABSYL ((p-dimethylamino-phenylazo) azobenzenesulfonyl), other azobenzene-sulfonyl groups, benzenesulfonyl groups, or arenesulfonyl groups, any of which may comprise substituents such as amino, dialkylamino, nitro, fluoro, and cyano groups; anthraquinone, nitrothiazole, and nitroimidazole compounds; rhodamine dyes (e.g., tetramethyl-6-carboxyrhodamine (TAMRA); ROX; cyanine; coumarin; BODIPY dyes; fluorescein dyes; and ALEXA dyes.

14. A composition according to claim 10, wherein Z is a fluorophore selected from fluorescein, 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), =2',7'-dimethoxy-4',5'-dichloro-6-carboxyfluorescein (JOE); Cy3, CY5, Cy5.5, a dansyl derivative; 6-carboxytetramethylrhodamine (TAMRA), a BODIPY fluorophore, tetrapropano-6-carboxyrhodamine (ROX), ALEXA dye, and Oregon Green.

15. A composition according to claim 10, wherein Z is a quencher selected from DABSYL (dimethylamino-azobenzene-sulfonyl) group, DANSYL (5-dimethylaminonaphthalenesulfonyl); DIMAPDABSYL ((p-dimethylamino-phenylazo) azobenzenesulfonyl), other azobenzene-sulfonyl groups, benzenesulfonyl groups, or arenesulfonyl groups, any of which may comprise substituents such as amino, dialkylamino, nitro, fluoro, and cyano groups; anthraquinone, nitrothiazole, and nitroimidazole compounds; rhodamine dyes (e.g., tetramethyl-6-carboxyrhodamine (TAMRA); ROX; cyanine; coumarin BODIPY dyes; fluorescein dyes; and ALEXA dyes.

* * * * *

UNITED STATES PATENT AND TRADEMARK OFFICE
CERTIFICATE OF CORRECTION

PATENT NO. : 7,745,614 B2
APPLICATION NO. : 11/218961
DATED : June 29, 2010
INVENTOR(S) : Eric Todd Kool It is certified that error appears in the above-identified patent and that said Letters Patent is hereby corrected as shown below:

In The Claims:

- In Claim 10, column 38 line 2: Please replace "awl" with --aryl--

Signed and Sealed this
Nineteenth Day of July, 2011

David J. Kappos
*Director of the United States Patent and Trademark Office*